US008129179B2

(12) United States Patent
Wikswo et al.

(10) Patent No.: US 8,129,179 B2
(45) Date of Patent: Mar. 6, 2012

(54) BIOREACTORS WITH AN ARRAY OF CHAMBERS AND A COMMON FEED LINE

(75) Inventors: John F. Wikswo, Brentwood, TN (US); David Cliffel, Nashville, TN (US); Eugene J. Leboeuf, Franklin, TN (US); Randall S. Reiserer, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1723 days.

(21) Appl. No.: 10/525,538

(22) PCT Filed: Aug. 27, 2003

(86) PCT No.: PCT/US03/26802
§ 371 (c)(1),
(2), (4) Date: Oct. 6, 2005

(87) PCT Pub. No.: WO2004/020573
PCT Pub. Date: Mar. 11, 2004

(65) Prior Publication Data
US 2006/0099705 A1    May 11, 2006

(51) Int. Cl.
*C12M 1/00* (2006.01)
*C12M 3/00* (2006.01)
*C12M 1/34* (2006.01)
*C12M 1/22* (2006.01)

(52) U.S. Cl. ............... 435/305.2; 435/288.3; 435/288.4; 435/288.5; 435/289.1; 435/297.5; 435/305.1; 435/287.3

(58) Field of Classification Search ..... 435/283.1–303.1
See application file for complete search history.

(56) References Cited

U.S. PATENT DOCUMENTS
2,157,438 A * 5/1939 Sparks .......................... 356/442
(Continued)

FOREIGN PATENT DOCUMENTS
WO       WO 01/07892 A1    2/2001
(Continued)

OTHER PUBLICATIONS
Harvath, L. et al, "Rapid quantitation of neutrophil chemotaxis; use of a polyvinylpyrrolidone-free polycarbonate membrane in multiwell assembly," *J. Immunol Method*, vol. 37, No. 1, 1980, pp. 39-45.
(Continued)

*Primary Examiner* — Nathan Bowers
*Assistant Examiner* — Lydia Edwards
(74) *Attorney, Agent, or Firm* — Tim Tingkang Xia, Esq.; Morris Manning & Martin, LLP

(57) ABSTRACT

A bioreactor (200) for cultivating living cells in a liquid medium. In one embodiment, the bioreactor (200) has a substrate (230) having a first surface and an opposite second surface, defining a channel (202) therein, and a plurality of chambers (204) formed in the substrate, wherein each of the plurality of chambers (204) is adapted for receiving cells in a liquid medium and formed with an open end (262), an opposite closed end (264) and side walls, the open end (262) and the closed end (264) defining a depth, d, therebetween for the corresponding chamber (206), the sidewalls defining a width, w, therebetween for the corresponding chamber (206). As such formed, each chamber (206) is in fluid communication with the channel (202) through the open end of the chamber (206), and at least two of the plurality of chambers (206) have depths or widths the same or different form each other.

69 Claims, 5 Drawing Sheets

U.S. PATENT DOCUMENTS

| | | | |
|---|---|---|---|
| 4,391,151 | A | 7/1983 | Nelson et al. |
| 4,988,623 | A | 1/1991 | Schwarz et al. |
| 5,376,548 | A | 12/1994 | Matsuo et al. |
| 5,443,985 | A | 8/1995 | Lu et al. |
| 5,489,515 | A | 2/1996 | Hatschek et al. |
| 5,520,787 | A * | 5/1996 | Hanagan et al. ......... 204/403.14 |
| 5,589,352 | A * | 12/1996 | Breznak et al. ................. 435/34 |
| 5,624,537 | A * | 4/1997 | Turner et al. ............... 422/82.01 |
| 5,635,358 | A | 6/1997 | Wilding et al. |
| 5,955,029 | A | 9/1999 | Wilding et al. |
| 6,124,138 | A | 9/2000 | Woudenberg et al. |
| 6,168,948 | B1 * | 1/2001 | Anderson et al. .......... 435/287.2 |
| 6,171,239 | B1 | 1/2001 | Humphrey |
| 6,197,575 | B1 * | 3/2001 | Griffith et al. ............. 435/288.4 |
| 6,267,858 | B1 | 7/2001 | Parce et al. |
| 6,391,558 | B1 * | 5/2002 | Henkens et al. ................. 435/6 |
| 6,440,645 | B1 | 8/2002 | Yon-Hin et al. |
| 2001/0044143 | A1 * | 11/2001 | Herman et al. ............... 435/174 |
| 2002/0025547 | A1 * | 2/2002 | Rao .............................. 435/40.5 |
| 2002/0058329 | A1 | 5/2002 | Singh et al. |
| 2002/0106786 | A1 | 8/2002 | Carcalho et al. |
| 2002/0164816 | A1 * | 11/2002 | Quake ........................... 436/161 |
| 2003/0003571 | A1 * | 1/2003 | Kanegasaki et al. ....... 435/288.5 |
| 2004/0142409 | A1 * | 7/2004 | Allen et al. ..................... 435/29 |
| 2006/0194273 | A1 * | 8/2006 | Thomas .......................... 435/29 |

FOREIGN PATENT DOCUMENTS

| | | | |
|---|---|---|---|
| WO | WO 02/46355 | * | 6/2002 |

OTHER PUBLICATIONS

Allen et al, "Improving the Next Generation of Bioartificial Liver Devices," Seminars in Cell & Developmental Biology, 13, 447-454, 2002.

Augenstein et al., "Effect of Shear on Death of Two Strains of Mammalian Tissue Cells," Biotechnol. Bioeng. , 13, 409-418, 1971.

Beeton et al., "A Novel Membrane Bioreactor for Microbial-Growth," Appl. Microbiol. Biotechnol. , 40, 812-817, 1994.

Bhujwalla et al., "Combined Vascular and Extracellular PH Imaging of Solid Tumors," NMR Biomed., 15,114-119, 2002.

Black et al., "Diblock Copolymers: Self-Assembly for Applications in Microelectronics," Encyclopedia of Materials : Science and Technology, Buschow, KHJ, ed. Elsevier, New York, 1-6, 2002.

Black et al., "Tuominen, M T. , Integration of Self-Assembled Diblock Copolymers for Semiconductor Capacitor Fabrication," Appl. Phys. Lett., 79, 409-411, 2001.

Borenstein et al., "Microfabrication Technology for Vascularized Tissue Engineering, Biomedical Microdevices," 4, 167-175, 2002.

Boyden, S., "The Chemotactic Effect of Mixtures of Antibody and Antigen on Polymorphonuclear Leucocytes," J. Exp. Med., 115, 453-466, 1962.

Brown et al., "Improvements to Parallel Plate Flow Chambers to Reduce Reagent and Cellular Requirements," BMC Immunology, 2, 9-16, 2001.

Cinamon et al., "A Real Time in Vitro Assay for Studying Leukocyte Transendothelial Migration Under Physiological Flow Conditions," J. Immunol. Methods, 273, 53-62, 2003.

De Bartolo et al., "A Novel Full-Scale Flat Membrane Bioreactor Utilizing Porcine Hepatocytes: Cell Viability and Tissue-Specific Functions," Biotechnol. Prog. , 16,102-108, 2000.

Ding et al., "Chemokines Stimulate Human T Lymphocyte Transendothelial Migration to Utilize VLA-4 in Addition to LFA-1," J. Leukoc. Biol., 69, 458-466, 2001.

Drioli et al., "Biocatalytic Membrane Reactors, Applications in Biotechnology and the Pharmaceutical Industry," Taylor & Francis, London, Philadelphia, 1999.

Dupin et al., "Impact of Colony Morphologies and Disinfection on Biological Clogging in Porous Media," Environ. Sci. Technol., 34, 1513-1520, 2000.

Dupin et al., "Mesoscale and Microscale Observations of Biological Growth in a Silicon Pore Imaging Element," Environ. Sci. Technol., 33, 1230-1236, 1999.

Falk et al., "A 48-Well Micro Chemotaxis Assembly for Rapid and Accurate Measurement of Leukocyte Migration," J. Immunol. Methods, 33, 239-247, 1980.

Fink et al., "Chronic Stretch of Engineered Heart Tissue Induces Hypertrophy and Functional Improvement," FASEB J., 14, 669-679, 2000.

Folkman et al., "Tumor Angiogenesis-Therapeutic Implications," N. Engl. J. Med., 285, 1182-1186, 1971.

Gillies et al., "MRI of the Tumor Microenvironment," J. Magn. Reson. Imaging, 16, 430-450, 2002.

Godbey et al., "In Vitro Systems for Tissue Engineering", Ann. N. Y. , Acad. Sci. , 961,10-26, 2002.

Griffith et al., "Tissue Engineering-Current Challenges and Expanding Opportunities," Science, 295, 1009-1014, 2002.

Griffith, L. G., "Emerging Design Principles in Biomaterials and Scaffolds for Tissue Engineering," Reparative Medicine: Growing Tissues and Organs, 961, 83-95, 2002.

Guarini et al., "Nanoscale Patterning Using Self-Assembled Polymers for Semiconductor Applications," J. Vac. Sci. & Tech. B, 19,2784-2788, 2001.

Guarini et al., "Optimization of Diblock Copolymer Thin Film Self Assembly," Advanced Materials, 14,1290-1294, 2002.

Guarini et al., "Process Integration of Self-Assembled Polymer Templates into Silicon Nanofabrication," Journal of Vacuum Science & Technology B, 20, 2788- 2792, 2002.

Hammer et al., "Measuring Receptor-Mediated Cell Adhesion Under Flow: Cell-Free Systems," Tissue engineering methods and protocols, Morgan, J. R. and Yarmush, M. L. , eds. Humana Press, Totowa, N. J., 543-552, 1999.

Heidemann et al., "Angiogenic Effects of Interleukin 8 (CXCL8) in Human Intestinal Microvascular Endothelial Cells Are Mediated by CXCR2," J. Biol. Chem., 278, 8508-8515, 2003.

Helmlinger, "Acid Production in Glycolysis-Impaired Tumors Provides New Insights into Tumor Metabolism," Clin. Cancer Res., 8, 1284-1291, 2002.

Higgs et al., "Regulation of Actin Filament Network Formation Through Arp2/3 Complex: Activation by a Diverse Array of Proteins," Annu. Rev. Biochem., 70, 649-676, 2001.

Hu et al., "Large-Scale Mammalian Cell Culture," Curr. Opin. Biotechnol., 8, 148-153, 1997.

Jackman et al., "Electrochemistry and Soft Lithography: A Route to 3-D," Chemtech, 29,18-30, 1999.

Jain et al., "Dissecting Tumour Pathophysiology Using Intravital Microscopy," Nature Reviews Cancer, 2, 266-276, 2002.

Jones et al., "P-Selectin Mediates Neutrophil Rolling on Histamine-Stimulated Endothelial Cells," Biophys. J., 65, 1560-1569, 1993.

Kaihara et al., "Silicon Micromachining to Tissue Engineer Branched Vascular Channels for Liver Fabrication," Tissue Eng., 6, 105-117, 2000.

Klemke et al., "CAS/Crk Coupling Serves As a "Molecular Switch" for Induction of Cell Migration," Journal of Cell Biology, 140, 961-972, 1998.

Labecki et al., "Protein Transport in Ultrafiltration Hollow-Fiber Bioreactors for Mammalian Cell Culture," Membrane Separations in Biotechnology, Wang, W. K. , ed., M. Dekker, New York, 1-62, 2001.

Ley, K., "The Selectins As Rolling Receptors," The selectins: initiators of leukocyte endothelial adhesion, Vestweber, D, ed. Harwood Academic Publishers, Australia, 63-104, 1997.

Li et al., "Cortactin Potentiates Bone Metastasis of Breast Cancer Cells," Cancer Res, 61, 6906-11, 2001.

Li et al., "Hexagonal Pore Arrays With a 50-420 Nm Interpore Distance Formed by Self-Organization in Anodic Alumina," J. Appl. Phys., 84, 6023-6026, 1998.

Li et al., "Initial Stages of Tumor Cell-Induced Angiogenesis: Evaluation Via Skin Window Chambers in Rodent Models," J Natl Cancer Inst, 92, 143-7, 2000.

Li et al., "On the Growth of Highly Ordered Pores in Anodized Aluminum Oxide," Chem. Mater. , 10, 2470-2480, 1998.

Lin et al., "Antiangiogenic Gene Therapy Targeting the Endothelium—Specific Receptor Tyrosine Kinase Tie2," Proc. Natl Acad Sci U S A, 95, 8829-34, 1998.

Lin et al., "*Inhibition of Tumor Angiogenesis Using a Soluble Receptor Establishes a Role for Tie2*," in Pathologic Vascular Growth, J Clin Invest, 100, 2072-8, 1997.

Lin et al., "*Inhibition of Tumor Growth by Targeting Tumor Endothelium Using a Soluble Vascular Endothelial Growth Factor Receptor*," Cell Growth Differ, 9, 49-58, 1998.

MacNeill et al., "*Toward a New Blood Vessel*," Vasc. Med., 7, 41-246, 2002.

Mansky et al., "*Controlling Polymer-Surface Interactions With Random Copolymer Brushes*," Science, 275,1458-1460, 1997.

Martinez et al., "*Acidic PH Enhances the Invasive Behavior of Human Melanoma Cells, Clinical & Experimental Metastasis*," 14, 176-186, 1996.

McDonald et al., "*Poly (Dimethylsiloxane) As a Material for Fabricating Microfluidic Devices*," Accounts of Chemical Research, 35,491-499, 2002.

McDuffie N. G. , Cell Culture Bioreactors. In : Bioreactor Design Fundamentals, Butterworth-Heinemann, Boston, 93-119,1991.

Millward et al., "*The Vortex Wave Membrane Bioreactor: Hydrodynamics and Mass Transfer*," Chemical Engineering Journal and the Biochemical Engineering Journal, 62, 175-181, 1996.

Mooney et al., "*Stabilized Polyglycolic Acid Fibre Based Tubes for Tissue Engineering*," Biomaterials, 17, 115-124, 1996.

Munn et al., "*Analysis of Cell Flux in the Parallel-Plate Flow Chamber-Implications for Cell Capture Studies*," Biophys. J., 67, 889-895, 1994.

Nollert et al., "*Hydrodynamic Shear-Stress and Mass-Transport Modulation of Endothelial-Cell Metabolism*," Biotechnol. Bioeng., 38, 588-602, 1991.

Papadaki et al., "*Quantitative Measurement of Shear-Stress Effects on Endothelial Cells*," Tissue engineering methods and protocols, Morgan, J. R. and Yarmush, M. L, eds. Humana Press, Totowa, N. J., 577-593, 1999.

Park et al., "*Integration of Cell Culture and Microfabrication Technology*," Biotechnol. Prog. , 19, 243-253, 2003.

Passeraub et al., "*Design, Microfabrication and Analysis of a Microfluidic Chamber for the Perfusion of Brain Tissue Slices*," Biomedical Microdevices, 5, 147-155, 2003.

Powers et al., "*A Microfabricated Array Bioreactor for Perfused 3D Liver Culture*," Biotechnol. Bioeng. , 78, 257-269, 2002.

Ramos et al., "*Quantitative Measurement of Cell-Cell Adhesion Under Flow Conditions*," Tissue engineering methods and protocols, Morgan, J. R. and Yarmush, M. L. , eds. Humana Press, Totowa, N. J., 507-519, 1999.

Renard et al., "*Induced Changes of Leukocyte Slow Rolling in an in Flow Pharmacological Model of Adhesion to Endothelial Cells*," Biorheology, 40,173-178, 2003.

Roth et al., "*Characterization of Transendothelial Chemotaxis of T Lymphocytes*," J. Immunol. Methods, 188, 97-116, 1995.

Schultz, "*Roles of Solute and Heat-Flow in the Development of Polymer Microstructure*," Polymer, 32,3268-3283, 1991.

Snyder et al., "*Fabrication of Multiple Microscale Features on Polymer Surfaces for Applications in Tissue Engineering*," Biomedical Microdevices, 3, 293-300, 2001.

Solan et al., "*Engineered Vessels: Importance of the Extracellular Matrix*," Transplant. Proc., 33, 66-68, 2001.

Tobert et al., "*Perfusion Culture Systems for Production of Mammalian Cell Biomolecules*," Large-Scale Mammalian cell culture, Feder, J. and Tolbert, W. R., eds., Academic Press, Orlando, 97-123, 1985.

Voisard et al., "*Potential of Cell Retention Techniques for Large-Scale High-Density Perfusion Culture of Suspended Mammalian Cells*," Biotechnol. Bioeng. , 82,751-765, 2003.

Walheim et al., "*Structure Formation Via Polymer Demixing in Spin-Cast Films*," Macromolecules, 30, 4995-5003,1997.

Weidner et al., "*Tumor Angiogenesis and Metastasis-Correlation in Invasive Breast-Carcinoma*," N. Engl. J. Med., 324, 1-8, 1991.

Whitesides et al. , Ingber, D. E., "*Soft Lithography in Biology and Biochemistry*," Annual Review of Biomedical Engineering, 3,335-373, 2001.

Wu et al. "*Fabrication of Complex Three-Dimensional Microchannel Systems in PDMS*," J. Am. Chem. Soc., 125, 554-559, 2003.

Xia et al., "*Soft Lithography*," Annual Review of Materials Science, 28,153-184, 1998.

Yao et al., "*Chemotaxis by A Cns Macrophage*," the Microglia, J. Neurosci. Res., 27, 36-42, 1990.

Jain et al., "*In Vitro and In Vivo Quantificatiaon of Adhesion Between Leukocytes and Vascular Endothelium*," Tissue engineering methods and protocols, Morgan, J.R. and Yarmush, M. L.., eds. Humana Press, Totowa, N. J., 553-575, 1999.

Jain, R. K., "*Angiogenesis and Lymphangiogensis in Tumors: Insights from Intravital Microscopy*," Cold Spring Harb. Symp. Quant. Biol., 67, 239-248, 2002.

Murdin et al., "*Immobilisation and Growth of Hybridomas in Packed Beds*," Bioreactors and Biotransformations, Moody, G. W. and Baker, P. B., eds. Elsevier Applied Science Publishers, London, New York, 99-110, 1987.

* cited by examiner

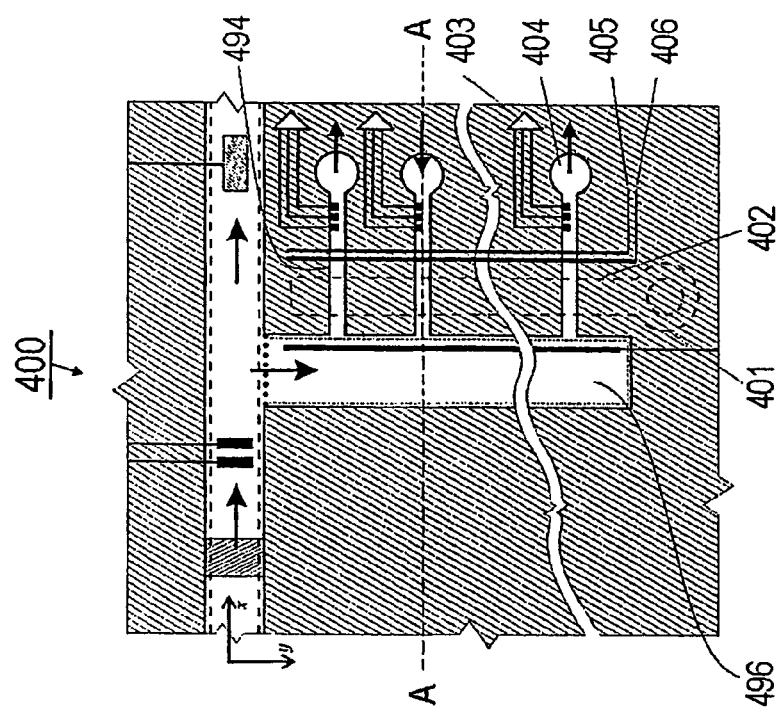
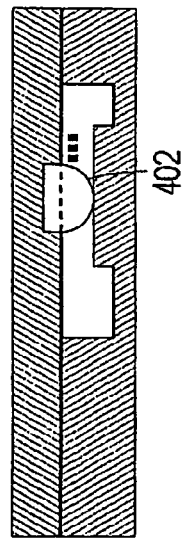
Fig. 3A
Fig. 3B

BIOREACTORS WITH AN ARRAY OF CHAMBERS AND A COMMON FEED LINE

The present invention was made with Government support under Grant No. N66001-01C-8064 awarded by the Defense Advanced Research Projects Administration and the Office of Naval Research. The present invention was also made with Government support under Grant 5R43 RR016124-02 awarded by the National Institute of Health. The United States Government has certain rights to this invention.

This application is being filed as a PCT International Patent application in the name of Vanderbilt University, a U.S. national corporation, applicant for the designation of all countries except the US, and John P. Wikswo and Franz J. Baudenbacher, U.S. nationals and residents, applicants for the designation of the US only, on 27 Aug. 2003.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. In terms of notation, hereinafter, "[n]" represents the nth reference cited in the reference list. For example, [11] represents the 11th reference cited in the reference list, namely, Hu, W. S. and Aunins, J. G., Large-Scale Mammalian Cell Culture, Curr. Opin. Biotechnol., 8, 148-153, 1997.

FIELD OF THE INVENTION

The present invention generally relates to an apparatus and methods for growing and maintaining a living system. More particularly, the present invention relates to an apparatus and methods that have a channel configuration allowing perfusate flow with diffusional exchange to tissue cells but no cell migration. Additionally, the present invention relates to an apparatus and methods that have capacity for growing and maintaining a living microorganism such as protozoa The present invention also relates to an apparatus and methods for dynamic analysis of a collection of cells such as a biofilm. More particularly, the present invention relates to an apparatus and methods for measuring response of a biofilm to one or more dynamic streams of substance such as chemical stressors at various depths of the biofilm.

Certain embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with multiple chambers and methods of using the same.

Certain other embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with an array of chambers with a common feed line and methods of using the same.

Certain additional embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise capillary perfused bioreactors and methods of using the same.

Certain further embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with substance injection capability and methods of using the same.

BACKGROUND OF THE INVENTION

Bioreactor is a device that can be used for culturing living cells. More particularly, bioreactors are vessels that provide a proper physical and chemical environment as well as fast transport of substrates and products to allow cellular biological reactions to occur, ideally rapidly and efficiently. The simplest bioreactor is a culture dish: In conventional cell culture using well-plates, culture-dishes, and flasks, the volume of the culture medium is typically 200 to 1000 times the volume of the cells. This ratio, when used in combination with buffering of the culture media, allows the cells to grow for at least 24 hours without media change. However, another consequence of this ratio is a corresponding dilution of whatever extracellular factors are produced by the cells and might otherwise provide paracrine cell-to-cell communication, which is possible in tissue because the extracellular volume might be only 10% of intracellular volume.

Much of the development of bioreactors was directed towards either the functional tissues, or the generation of biochemicals and pharmaceuticals. For example, over the last 20 years studies on the generation of skin, pancreas, cartilage, liver, cornea and bladder have taken particular importance[1]. In the United States alone, there are more than 80,000 individuals waiting for an organ transplant, and hence the need to develop improved bioreactor technology is self-evident. There is also a growing recognition that progress in understanding cell motility and chemotactic signaling, as well as other complex cellular processes, is often constrained by the laboratory techniques available for observing and intervening at various points in the processes. Many of these processes can be examined best in a properly instrumented bioreactor.

There is a wide variety in bioreactors, including stirred vessels, bubble column, packed beds[2], air-lift reactors, and membrane reactors[3] that include plates, rotating plates, spiral-wound and hollow fibres. Hollow-fiber reactors are of special importance since (depending of their structure) they may allow as much as 30,000 $m^2$ of membrane area per $m^3$ module volume[4-6]. However, given that mammalian cells are very sensitive to shear forces[7-9] (which originate mainly from agitation and aeration), it is important to reduce the forces as much as possible in the reactor where the cells will be grown[9,10]. Membranes have been used in bioreactors to increase survival of cells. For instance, it has been known that liquid-gas interface created in some models of reactors is particularly damaging for mammalian cells. That potentially lethal interface can be eliminated by the use of a hydrophobic membrane[9].

Bioreactors may be also classified by means of their mode of operation: batch, fed-batch and continuous cultivation (also called perfused cultivation). In the first or batch mode, no substrate is added, nor medium removed; in the case of the fed-batch mode there is a continuous feeding, but nothing is removed until the reactions are terminated and the reactor emptied. While these systems imply a low effort for process control, the productivity is low compared to that in perfused systems, the third mode, where a permanent inflow of substrate and outflow of medium takes place. Besides the high productivity, there is a better cell physiology control in this kind of reactors[11] and in the case of mammalian cell culture, it has been shown to provide significant advantage over static methods[12,13].

One of the limitations when developing large three-dimensional tissues is the lack of a proper vascular supply for nutrient and metabolite transport. A number of studies have analyzed the artificial vascular networks[14-18], and there have been a number of attempts to construct functional microfabricated scaffolds[3,16,19-21]. The techniques by which these networks have been produced include plasma etching, photolithography, soft lithography, microcontact printing, microfluidic patterning using microchannels, laminar flow patterning and stencil patterning[22-25]. In the case of plasma etching technologies we can consider the high aspect ratio micromachining (HARMS) as a very powerful tool since it allows to etch channels of virtually unlimited depth without increasing the width already achieved by lithography[22]. It is also possible to construct three dimensional microchannel systems in PDMS with complex topologies and geometries[15].

Additionally, one needs to realize that the growth of clinically-implantable tissue may require the ultimate biodegradation and the mechanical properties of the tissue scaffold[16]. These properties are directly related to the crystallinity, molecular weight, glass transition temperature and monomer hydrophobicity of the materials chosen to fabricate the tissue[19]. Naturally derived materials such as collagen have been employed[26], as well as synthetic and semi synthetic ones. Polyglycolic acid (PGA) possesses high porosity and it makes easy the fabrication of devices, therefore, PGA fibre meshes have been considered to transplant cells. However, they cannot resist significant compressional forces. An alternative to solve this problem is to use polymers of lactic and glycolic acid whose ratios can be adjusted to control the crystallinity of the material and hence the degradation rate and mechanical properties. Fibre-based tubes have been fabricated from these polymers[27].

It is important to compare the vascular nature of living tissue with the capabilities provided by existing microfabricated cell-perfusion bioreactor systems. In tissue, arteries divide into progressively smaller vessels, eventually reaching arterioles and then capillaries. The arterioles are important because they contain the precapillary sphincters, which allow control of the perfusion of individual capillary beds, but also provide the majority of the peripheral resistance and hence the pressure drop associated with the arterial supply. As a result, the pressure difference across the capillary endothelium membrane is kept sufficiently low to allow diffusional transport of nutrients and metabolites across the membrane, as well as the trafficking of immune cells required for tissue maintenance and infection control. Were the pressures in the capillaries as high as those in the arterioles, the capillary wall thickness would be too great to allow these critical transport phenomena. The venous return system is in many ways a mirror of the arterial system, albeit at lower pressures. Another feature of the living vascular system is that the branching process described above allows all cells to be within 50 to 200 microns of a capillary, depending upon the specific tissue. As a result, the arterial supply and venous return systems are intercalated in such a manner that every capillary that perfuses a large group of cells is connected to the larger supply and return systems with a self-similarity that ensures uniform perfusion and transcapillary pressures. It is this intercalation process that is so difficult to replicate with microfabrication. For example, Borenstein et al.,[22] describe a process to build a two-dimensional vascular system that could create a multi-scale perfusion system for supporting endothelial cells, but there is no provision to selectively limit diffusive transport across the smallest capillaries to perfuse cells lying outside of the perfusion network. More importantly, the networks they show have a large region of the device that is covered with the larger vessels, and the region of the bioreactor that is limited to capillary vessels is in fact quite small.

Thus, there is a need for microfabricated migration bioreactors that mimic in vitro the microenvironments of normal tissue was well as that of tumors, infected tissue, and wounded tissue, while providing independent control of chemokine and growth factor gradients, shear forces, cellular perfusion, and the permeability of physical barriers to cellular migration, thereby allowing detailed optical and electrochemical observation of normal, immune, and cancerous cells during cell migration, intravasation, extravasation, and angiogenesis. Angiogenesis, tumor metastasis, and leukocyte infiltration into tissue are complex processes that are regulated not only by cellular responses to a single chemokine, but also by external factors, such as multiple competing chemokine and growth factor signals, autocrine feedback loops, cell-cell interactions, and mechanical forces such as vessel shear stress. Current approaches for assessing migration across cellular barriers include Boyden and transwell chambers that provide an integrated fluorescence assay of migration across filters to allow quantitation of migration[28-34], parallel plate flow chambers[35-38], in which adhesion and rolling on endothelial cells in shear stress can be assessed[35,39-44], and in vivo intravital microscopy in which migration of cells in living animals is visualized[45-48]. Each of these approaches has limitations, including the inability to have sustained and controlled chemotactic gradients (all systems), the inability to visualize migration in real time or with physiologic shear stress (Boyden and transwell chambers), the inability to observe extravasation or angiogenesis into an underlying, deep cellular matrix (parallel plate flow chambers) and the inability to control all aspects of the experiments, e.g., having defined cell populations and controlled microfluidics for independent control of shear and tissue perfusion (all systems, especially intravital microscopy). The development of a motility/metastasis model system with independent control of endothelial shear stress, chemokine gradients, tissue perfusion, and the ability to add different cell types through different ports, combined with state-of the art imaging techniques and sensor capabilities would represent a huge advance over currently available systems.

Indeed, the need for such capabilities is quite urgent. Angiogenesis is a dynamic process, influenced by the cellular microenvironment and intricately linked to metastasis[49,50]. It has been demonstrated that both VEGF and angiopoietin/tyrosine kinase (Ang/Tie2) function are required for tumor angiogenesis[51-53]. However, how signals from those two receptor systems are integrated to mediate angiogenesis has not been determined, in part due to the lack of good model systems. The next step would be to study the coordination and integration of VEGF and Ang signaling in endothelial cell migration, vascular sprouting and maturation, and tumor transendothelium migration. As with angiogenesis, multiple environmental inputs affect tumor metastasis and leukocyte infiltration. Activation of one chemokine receptor in tumor cells affects the induction of other ligands and receptors in tumor cells as well as endothelial cells and leukocytes, but the mechanism is poorly understood[54]. There is a need for an understanding of how alteration of chemokine receptor internalization and/or changes in receptor association with adaptor molecules such as AP-2 or beta-arresting affect chemokine receptor activity as tumor cells move through a complex matrix. How external factors such as cell-cell adhesion, cell-matrix interactions, and vessel shear stress affect cytoskeletal reorganization during migration through tissues is also poorly understood. Cortactin overexpression increases the metastasis of breast cancer cells to bone[55], however the mechanism remains unclear. Likewise, lack of WASp protein in humans leads to an X-linked immune disorder that may result from signaling, proliferation or chemotaxis defects[56]. There is a need to study the role of cortactin and WASp proteins in chemotaxis of breast cancer and HL60 cells in a complex multicell environment involving controllable shear, cell-cell interactions, and chemokine gradients. As a final example, matrix metalloproteinases (MMPs) are extracellularly expressed enzymes found in many types of cancer and are thought to be important in tumor development, growth, invasion and metastasis. It has recently been discovered that skin tumors that develop in mice deficient for MMP-3 (MMP-3 null mice) progress and grow much faster than skin tumors from normal, wild-type mice. This difference is associated with a reduced number of immune cells in the tumor and surrounding tissue in the MMP-3 null mice. The logical progression of this research is to determine how loss of an MMP affects the ability of immune cells, namely monocytes and neutrophils, to infiltrate from the peripheral blood circulation to the tumor site. The ability to control the experimental environment, including multiple defined cell populations, is critical to elucidate the relative importance of tumor-host interactions in MMP-3 induced cellular chemotaxis.

Despite the progress made over the years, however, currently available bioreactors cannot provide a more physiologic environment that would include a three-dimensional in vitro region with multiple cell types, stimuli, and measurement capabilities and allows study of molecular aspects of the chemotactic response. Thus, bioreactors that mimic in vitro the microenvironments of tumors and tissue while providing independent control of chemokine and growth factor gradients, shear forces, cellular perfusion, and the permeability of physical barriers to cellular migration, thereby allowing detailed optical and electrochemical observation of normal and cancerous cells during cell migration, intravasation, extravasation, and angiogenesis need to be developed.

Therefore, a heretofore unaddressed need exists in the art to address the aforementioned deficiencies and inadequacies.

SUMMARY OF THE INVENTION

In one aspect, the present invention relates to a bioreactor for cultivating living cells in a liquid medium. In one embodiment, the bioreactor has a substrate having a first surface and an opposite second surface, defining a channel therein, and a plurality of chambers formed in the substrate, wherein each of the plurality of chambers is adapted for receiving cells in a liquid medium and formed with an open end, an opposite closed end and side walls, the open end and the closed end defining a depth, d, therebetween for the corresponding chamber, the sidewalls defining a width, w, therebetween for the corresponding chamber. As such formed, each chamber is in fluid communication with the channel through the open end of the chamber, and at least two of the plurality of chambers have depths or widths same or different from each other.

The substrate can be fabricated from glass, Mylar, PDMS, silicon, a polymer, a semiconductor, or any combination of them.

An inlet port is formed in fluid communication with the channel, and an outlet port is formed in fluid communication with the channel as well, wherein the inlet port and the outlet port are apart from each other along the channel.

Each of the plurality of chambers is adapted to receive and culture at least one predetermined type of cells. The cells can be any type of living cells, including, but not limited to, bacteria, protozoa, or both, normal cells, tumor cells, or any combination of them. The cells can be in a collection, or in the form of a biofilm.

The bioreactor further has a barrier for at least one of the chambers, wherein the barrier is positioned at the open end of the corresponding chamber and has a porosity to allow the corresponding chamber and the channel in fluid communication and allow at least one predetermined type of cells to permeate between the corresponding chamber and the channel and at least another predetermined type of cells not to permeate between the corresponding chamber and the channel. Thus, the barrier has a selective porosity for the cells.

The bioreactor also includes a biocompatible coating layer applied to the channel walls, wherein the biocompatible coating layer comprises a material that may inhibit cell adhesion to the biocompatible coating layer to keep the fluid communication in the channel open. Alternatively, the biocompatible coating layer comprises a material that may enhance cell adhesion to the biocompatible coating layer, or function as a fluorescent marker or indicator of the state of cells.

The bioreactor also includes a biocompatible coating layer applied to the sidewalls of each chamber, wherein the biocompatible coating layer comprises a material that may inhibit cell adhesion to the biocompatible coating layer, enhance cell adhesion to the biocompatible coating layer, or function as a fluorescent marker or indicator of the state of cells.

At least one auxiliary port and an auxiliary channel are formed in the substrate, wherein the auxiliary channel is in fluid communication with the auxiliary port and a corresponding one of the chambers for allowing individual control of the environment of the corresponding chamber. The individual control of the environment of the corresponding chamber includes any and all intended activities that may affect the environment of a chamber such as the delivery or removal of the cells, fluids or chemicals to the corresponding chamber or flushing the corresponding chamber.

Optionally, at least one sample chamber and a plurality of sample channels are formed in the substrate, wherein the plurality of sample channels are in fluid communication with the sample chamber and a corresponding chamber. As formed, the sample chamber is in fluid communication with at least one corresponding auxiliary channel that is in fluid communication with at least one corresponding auxiliary port, for allowing individual control of the environment of the corresponding sample chamber. The individual control of the environment of the corresponding sample chamber includes any and all intended activities that may affect the environment of a sample chamber such as the delivery or removal of the fluids or chemicals to the corresponding sample chamber. The sample chamber is further adapted for receiving a sample of host material, such as soil, that provides exudates affecting the cells or biofilm in the corresponding chamber, and the sample chamber is formed with a closed end and an opposite open end through which the host material can be received into or removed from the sample chamber. Additionally, a lid adapted for slidably covering or opening the open end of the sample chamber can be utilized.

Alternatively, at least such a sample chamber can be formed in the substrate such that the sample chamber is directly in fluid communication with a corresponding chamber, and adapted for receiving a sample of host material that affects the cells or biofilm in the corresponding chamber.

The bioreactor additionally includes means adapted for electrochemical measurements of the cells responsive to the liquid medium in at least one of the chambers. In one embodiment, the means for electrochemical measurements includes a reference electrode, a counter electrode, a plurality of electrically conductive leads, where a first electrically conductive lead electrically couples the reference electrode to a corresponding edge connector pad, and a second electrically conductive lead electrically couples the counter electrode to a corresponding edge connector pad. The means for electrochemical measurements can also be used to measure the electrochemical constituents outside the cells that reflect the status of the cells, the culture medium, or the cellular exudates.

The means for electrochemical measurements further includes a plurality of individually addressable working electrodes and a plurality of corresponding amplifiers, each individually addressable working electrode being electrically coupled to a corresponding amplifier through a corresponding electrically conductive lead, wherein the liquid medium includes at least one or more analytes, and wherein the plurality of individually addressable working electrodes are adapted for capable of sensing the concentration of a single analyte of the liquid medium at multiple locations in a corresponding chamber or the concentrations of a plurality of analytes of the liquid medium at multiple locations in the corresponding chamber at a time period shorter than a characteristic reaction time related to at least one of cellular physiological activities of the cells. Additionally, the plurality of individually addressable working electrodes are further adapted for capable of measuring the metabolic variables related to the cells responsive to the liquid medium at multiple locations in the corresponding chamber at a time period shorter than a characteristic reaction time related to at least one of cellular physiological activities of the cells.

The bioreactor further includes a plurality of electrically conductive output leads, each electrically coupling a corresponding amplifier to an output device such as a multiplexed potentiostat.

Alternatively, the bioreactor additionally includes a plurality of controlling ports and a plurality of connection channels, wherein each of the connection channels is in fluid communication with a corresponding controlling port and the chamber. The bioreactor further includes a fluid control valve adapted for controlling the fluid communication between the plurality of controlling ports and the chamber, wherein the fluid control valve includes a pneumatic or mechanical valve. A control port adapted for controlling the fluid control valve can also be provided.

In this embodiment, the counter electrode and the reference electrode can be positioned between the fluid control valve and the plurality of controlling ports, wherein the liquid medium includes at least one or more analytes, and wherein the plurality of individually addressable working electrodes are positioned between the fluid control valve and the plurality of controlling ports and adapted for capable of sensing the concentration of a single analyte of the liquid medium corresponding to multiple locations in a corresponding chamber, or the concentrations of a plurality of analytes of the liquid medium corresponding to multiple locations in the corresponding chamber, at a time period shorter than a characteristic reaction time related to at least one of cellular physiological activities of the cells. The plurality of individually addressable working electrodes are further adapted for capable of measuring the metabolic variables related to the cells responsive to the liquid medium at multiple locations corresponding to the corresponding chamber, at a time period shorter than a characteristic reaction time related to at least one of cellular physiological activities of the cells.

The bioreactor further includes a plurality of electrically conductive output leads, each electrically coupling a corresponding amplifier to an output device such as a multiplexed potentiostat.

In one embodiment, the reference electrode can be strategically positioned as a common reference electrode and adapted for electrochemical measurements of the cells responsive to the liquid medium in the plurality of chambers. Correspondingly, in each of the plurality of chambers, a counter electrode is adapted for electrochemical measurements of the cells responsive to the liquid medium in a corresponding chamber to allow the plurality of chambers to be operated individually and the means for electrochemical measurements for the plurality of chambers to be activated for one or more chambers at a time sequentially.

The bioreactor further includes means positioned in the channel and adapted for monitoring of the cells therein optically, electrically or both. In one embodiment, the means for monitoring of the cells can include at least one optical sensor and at least one lead in optical communication with a corresponding optical sensor. The optical sensor includes at least one device selected from the group of an LED and photodiode pair, a fiber optic coupler, and an optical detecting head. Other optical devices can b utilized as well. Alternatively, the means for monitoring of the cells includes at least one electrical sensor and at least one lead in electrical communication with a corresponding electrical sensor. Such monitoring means can also be utilized to monitor other dynamic activities in the channel, for example, activities and responses of cells when a bolus of selected chemicals moves along the channel.

In another aspect, the present invention relates to a bioreactor for cultivating living cells in a liquid medium. In one embodiment, the bioreactor has a substrate having a first surface and an opposite second surface and a plurality of array of chambers formed on the substrate. Each array of chambers is adapted for receiving cells in a liquid medium and including a channel and a plurality of chambers formed in the substrate, wherein each of the plurality of chambers is adapted for receiving cells in a liquid medium and formed with an open end, an opposite closed end and side walls, the open end and the closed end defining a depth, d, therebetween for the corresponding chamber, the sidewalls defining a width, w, therebetween for the corresponding chamber, and the chamber being in fluid communication with the channel through the open end, and wherein at least two of the plurality of chambers have depths or widths same or different from each other. Each array of chambers can be formed according to the embodiments set forth above.

In yet another aspect, the present invention relates to a method for culturing a plurality of biofilms, each containing a predetermined type of cells or cell growth conditions. In one embodiment, the method includes the steps of providing a bioreactor that has a substrate having a first surface and an opposite second surface and a plurality or array of chambers formed on the substrate, each being adapted for receiving cells in a liquid medium and including a channel and a plurality of chambers formed in the substrate, wherein each of the plurality of chambers is adapted for receiving cells in a liquid medium and formed with an open end, an opposite closed end and side walls, the open end and the closed end defining a depth, d, therebetween for the corresponding chamber, the sidewalls defining a width, w, therebetween for the corresponding chamber, and the chamber being in fluid communication with the channel through the open end, and wherein at least two of the plurality of chambers have depths or widths same or different from each other, and culturing at least two biofilms in at least two arrays of chambers of the bioreactor.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIGS. 3A-B shows a bioreactor with a common feed line according to yet another embodiment of the present invention: 3A, a cross-sectional partial view, 3B, a cross-sectional side view along line A-A in FIG. 3A.

DETAILED DESCRIPTION OF THE INVENTION

Figures 1A, 1B:
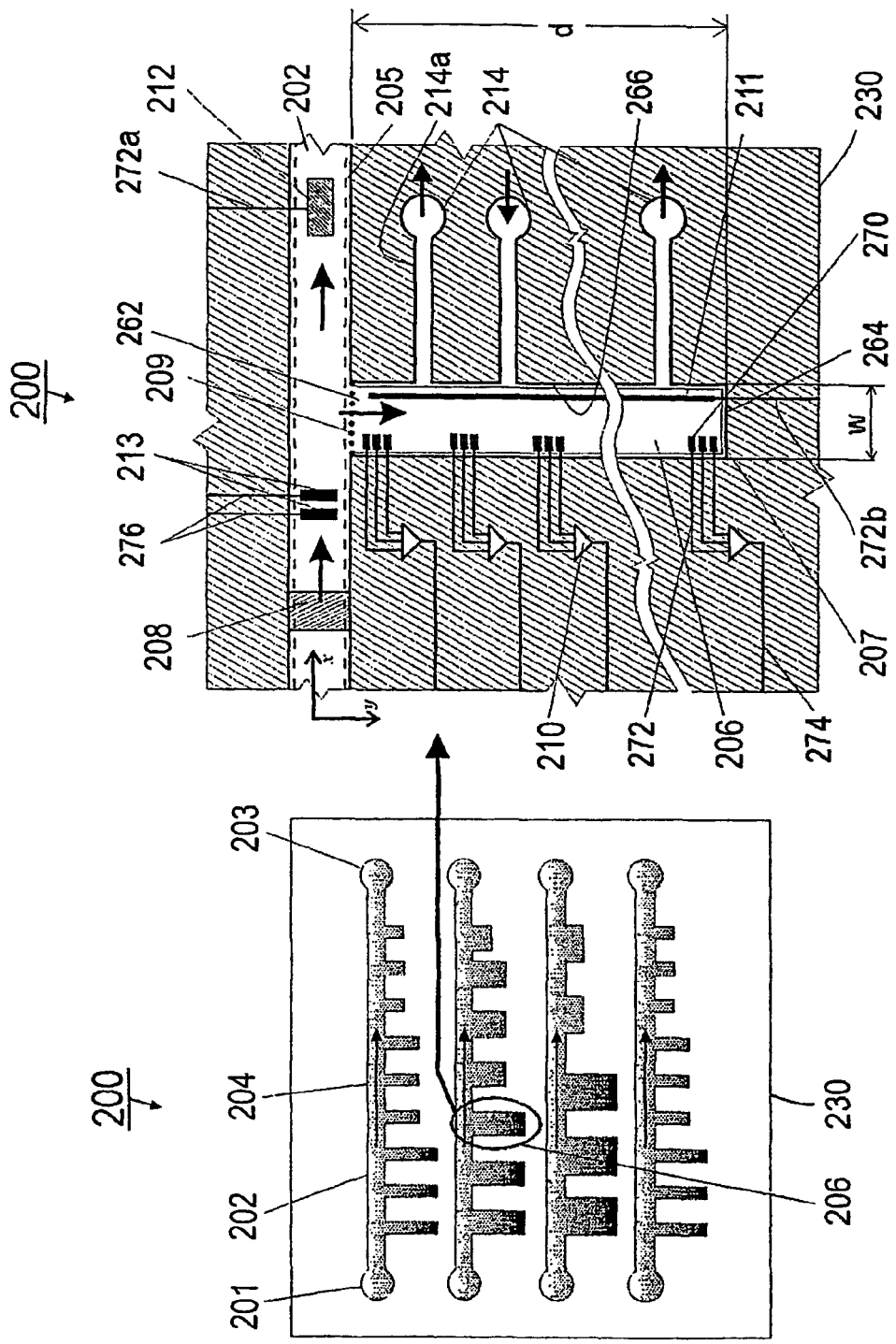
FIG. 1A schematically shows a bioreactor with a common feed line according to one embodiments of the present invention.
FIG. 1B shows a cross-sectional partial view of a bioreactor as shown in FIG. 1A.

Various embodiments of the invention are now described in detail. Referring to the drawings, like numbers indicate like parts throughout the views unless the context clearly dictates otherwise. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

DEFINITIONS

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis. Molecular Cloning: A Laboratory Manual, Second Edition (1989) Cold Spring Harbor Laboratory Press, Cold Spring Harbor, New York (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). See also, PCR Protocols: A Guide to Methods and Applications, Innis et al., eds., Academic Press, Inc., New York (1990); Saiki et al., Science 1988, 239:487; and PCR Technology: Principles and Applications for DNA Amplification, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. As used herein, a cell is generally living unless otherwise indicated. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). Cell or a plurality of cells can also comprise cell lines. Example of cell lines include liver cell, macrophage cell, neuroblastoma cell, endothelial cell, intestine cell, hybridoma, CHO, fibroblast cell lines, red blood cells, electrically excitable cells, e.g. Cardiac cell, myocytes (AT1 cells), cells grown in co-culture, NG108-15 cells (a widely used neuroblastoma X glioma hybrid cell line, ATCC# HB-12317), primary neurons, a primary cardiac myocyte isolated from either the ventricles or atria of an animal neonate, an AT-1 atrial tumor cardiac cell, Liver cells are also known as Hepatocytes, Secretory cell (depolarize and it secretes things) pancreatic beta cells secrete insulin, HELA cells (Helen Lane), HEK293

Human Epithial Kidney c, Erythrocytes (primary red blood cells), Lymphocytes and the like. Each cell line may include one or more cells, same or different. For examples, the liver cell comprises at least one of Human hepatocellular carcinoma ("HEPG2") cell, CCL-13 cell, and H4IIE cell, the macrophage cells comprises at least one of peripheral blood mononuclear cells ("PBMC"), and skin fibroblast cells, the neuroblastoma cell comprises a U937 cell, the endothelial cell comprises a human umbilical vein- endothelial cell ("Huv-ec-c"), and the intestine cell comprises a CCL-6 cell.

"Culture" means a growth of living cells in a controlled artificial environment. It may be a culture of microorganisms, such as a bacterial culture, or one of animal or plant cells, such as a tissue culture. The bioreactors according to the invention can do both and more. Cultures require appropriate sources of food and energy, provided by the culture medium, and a suitable physical environment. Tissue cultures can themselves become a culture medium for viruses, which grow only with live cells. Cultures of only one kind of cells are known as pure cultures, as distinguished from mixed or contaminated cultures.

"Tissue" means an aggregation of cells more or less similar morphologically and functionally. The animal body is composed of four primary tissues, namely, epithelium, connective tissue (including bone, cartilage, and blood), muscle, and nervous tissue. The process of differentiation and maturation of tissues is called histogenesis.

A "sensor" is broadly defined as any device that can measure a measurable quantity. For examples, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, any combination of them and the like. A variety of sensors can be chosen to practice the present invention.

The term "analyte" means a material that can be consumed or produced by a cell. Examples of analyte of interest include pH, K, oxygen, lactate, glucose, ascorbate, serotonin, dopamine, ammonina, glutamate, purine, calcium, sodium, potassium, NADH, protons, insulin, NO (nitric oxide) and the like.

The term "flow" means any movement of fluid such as a liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a substrate on microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

A "liquid or medium" is a fluid that may contain one or more substances that affecting growth of cells, one or more analytes, or any combination of them. A medium can be provided with one or more analytes to be consumed by one or more cells. A medium can have one or more analytes generated by one or more cells. A medium can also have at the same time one or more analytes to be consumed by one or more cells and one or more analytes generated by one or more cells. A medium may consist of natural materials, such as enzymatic digests, extracts of yeast or beef, milk, potato slices, or chick embryos. Artificial media are prepared by mixing various ingredients according to particular formulas. A complex medium contains at least one crude ingredient derived from a natural material, hence of unknown chemical composition. A chemically defined or synthetic medium is one in which the chemical structure and amount of each component are known.

An "inlet region" is an area of a bioreactor that receives molecules or cells or liquid. The inlet region may contain an inlet port and channel, a well or reservoir, an opening, and other features which facilitate the entry of molecules or cells into the device. A bioreactor may contain more than one inlet region if desired. The inlet region is in fluid communication with the channel and is upstream therefrom.

An "outlet region" is an area of a bioreactor that collects or dispenses molecules or cells or liquid. An outlet region is downstream from a discrimination region, and may contain outlet channels or ports. A bioreactor may contain more than one outlet region if desired.

An "analysis unit" is a microfabricated substrate, e.g., a microfabricated chip, having at least one inlet region, at least one channel and chamber, at least one detection region and at least one outlet region. A device of the invention may comprise a plurality of analysis units.

A "channel" is a pathway of a bioreactor of the invention that permits the flow of molecules or cells to pass a detection region for detection (identification), or measurement. The detection and discrimination regions can be placed or fabricated into the channel. The channel is typically in fluid communication with an inlet port or inlet region, which permits the flow of molecules or cells or liquids into the channel. The channel is also typically in fluid communication with an outlet region or outlet port, which permits the flow of molecules or cells or liquid out of the channel. The channel can also be used as a chamber to grown cells, and vice versa.

A "detection region" or "sensing volume" or "chamber" is a location within the bioreactor, typically in or coincident with the channel (or a portion thereof) and/or in or coincident with a detection loop, where molecules or cells to be grown, identified, characterized, hybridized, measured, analyzed or maintained (etc.), are examined on the basis of a predetermined characteristic. In one embodiment, molecules or cells are examined one at a time. In other embodiments, molecules, cells or samples are examined together, for example in groups, in arrays, in rapid, simultaneous or contemporaneous serial or parallel arrangements, or by affinity chromatography.

"Reaction time" is the time that a system of interest requires to respond to a change. For example, the reaction time of a cell is the time required for at least one of the physiological processes of a cell to adapt or respond to a change in its environment. Each type of cell has its own characteristic reaction time with respect to a particular change in its environment. The reaction time of a sensor is the time required for the sensor to respond to a change in the quantity that it is sensing. For example, the reaction time of an electrochemical sensor is set by the size of the sensor and the thickness and nature of protective coatings on the activated surfaces of the sensor. The reaction time of a microfluidic system is determined by, among other things, the reaction time of the cell to changes in the environment, the time required for chemical species to diffuse throughout the sensing volume, the reaction time of the sensor(s) and the diffusion time of the analyte being controlled by the actuators.

"Bacteria" are extremely small—usually 0.3-2.0 micrometers in diameter—and relatively simple microorganisms possessing the prokaryotic type of cell construction. Each bacterial cell arises either by division of a preexisting cell with similar characteristics, or through combination of elements from two such cells in a sexual process.

"Protozoa" means a group of eukaryotic microorganisms traditionally classified in the animal kingdom. Although the name signifies primitive animals, some Protozoa (phytoflagellates and slime molds) show enough plantlike characteristics to justify claims that they are plants. Protozoa range in size from 1 to $10^6$ micrometers. Colonies are known in flagellates, ciliates, and Sarcodina. Although marked differentiation of the reproductive and somatic zooids characterizes certain colonies, such as *Volvox,* Protozoa have not developed tissues and organs.

Several embodiments are now described with reference to the FIGS. 1-5, in which like numbers indicate like parts throughout the FIGS. 1-5.

OVERVIEW OF THE INVENTION

The inventors of the present invention overcome the disadvantages of the prior art and develop new bioreactors that have, among other new and inventive features, the capability of providing controlled chemokine gradients independent of the perfusion flow and allow extravasation of a cellular matrix. Recent advances in the fabrication of nanofilters[57-61] are used to create perfused-membrane bioreactors according to the present invention that allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment.

One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence, the bioreactors according to the present invention can be considered as the next generation of migration bioreactors that may move beyond a simple MicroTransWell (MTW) system to one that more closely replicates in vitro the microenvironment living tissue.

Moreover, the application of microfabrication techniques, microfluidics, and microbiosensors with the bioreactors according to the present invention offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These devices will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Additionally, the limitation of the planar Borenstein design that there is too little surface area of capillaries available to support the growth of a substantial volume of cells is overcome by the present invention, which remedies this problem by creating a multi-layer intercalated supply and return bioreactor that allows the full surface of a planar bioreactor to be covered with capillaries, and hence capillary-perfused cells.

More specifically, in one aspect, the present invention relates to bioreactors. These bioreactors are biomicroelectromechanical systems (BioMEMS) that serve as migration microenvironments to study molecular mechanisms of tumor angiogenesis, tumor metastasis and leukocyte migration, but can also function as more general tissue bioreactors and perfusion systems. Among other things, one unique aspect of these microfluidic devices is their integration of suitable cell culture and microfabrication techniques, which permit cell growth in small, confined, well-perfused volumes at tissue densities, provide independent control of multiple chemokines and growth factor gradients, shear forces, tissue perfusion, and permeability of physical barriers to cellular migration, and allow detailed optical and electrochemical observation of normal and cancerous cells during cell migration, intravasation, extravasation, angiogenesis, and other cellular processes.

Recent advances in the fabrication of nanofilters[57-61] can be used to practice the present invention to provide perfused-membrane bioreactors that can allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment. One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence the next generation of migration bioreactors will eventually move beyond a simple MicroTransWell (MTW) system to one that more closely replicates in vitro the microenvironment living tissue.

The application of microfabrication techniques, microfluidics, and microbiosensors offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These bioreactors will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Without intent to limit the scope of the invention, exemplary devices, application of them and related observations according to the embodiments of the present invention are given below. Note that titles or subtitles may be used in the examples for convenience of a reader, which in no way should limit the scope of the invention. Moreover, certain theories may have been proposed and disclosed herein; however, in no way they, whether they are right or wrong, should limit the scope of the invention so long as the devices and applications of them are practiced according to the invention without regard for any particular theory or scheme of action.

Referring now to FIGS. 1-5, the present invention can be practiced in association with an inventive bioreactor 200 as shown in FIGS. 1-5. In one embodiment, referring first to FIGS. 1A and 1B, the bioreactor 200 includes a substrate 230 having a first surface and an opposite second surface. The bioreactor 200 has a plurality of array of chambers 204 formed on the substrate 230. Each array of chambers 204 is adapted for receiving cells in a liquid medium and includes a channel 202 and a plurality of chambers 206 formed in the substrate 230. Each of the plurality of chambers 206 is adapted for receiving cells in a liquid medium and formed with an open end 262, an opposite closed end 264 and sidewalls 266. The open end 262 and the closed end 264 of a particular chamber 206 define a depth, d, therebetween for the corresponding chamber 206, which is in fluid communication with the channel 202 through the open end 262. Additionally, the sidewalls 266 defines a width, w, therebetween for the corresponding chamber 206. As formed, at least two of the plurality of chambers 206, either from same array or different arrays, may have depths or widths same or different from each other. This design allows the bioreactor 200 to provide a variety of environments to cells tailored for different applications. The substrate 230 can be fabricated from glass, Mylar, PDMS, silicon, a polymer, a semiconductor, or any combination of them.

Each array of chambers 204 may further includes an inlet port 201 formed in fluid communication with the channel 202, and an outlet port 203 formed in fluid communication with the channel 202, wherein the inlet port 201 and the outlet port 203 are apart from each other along the channel 202. As such formed, a fluid or an intended amount of material such as a bolus of selected chemicals 206 can be introduced from an external device or port (not shown) into the channel 202 through the inlet port 201, and away from the channel 202 through the outlet port 203. Thus, to each array 204, channel 202 serves as a common feed line to the plurality of chambers 206.

Each of the plurality of chambers 206 is adapted to receive and culture at least one predetermined type of cells. The cells can be any type of living cells, including, but not limited to, bacteria, protozoa, or both, normal cells, tumor cells, or any combination of them. Cells can be introduced into a chamber individually, in a collection of cells, or in the form of biofilms. Different chambers can have same or different types of cells.

The bioreactor 200 further includes a barrier 209 for at least one of the chambers 206, wherein the barrier 209 is positioned substantially at the open end 262 of a corresponding chamber 206 as shown in FIG. 1B. The barrier 209 has a porosity to allow the corresponding chamber 206 and the channel 202 in fluid communication to each other. The barrier 209 also allows at least one predetermined type of cells to permeate between the corresponding chamber 206 and the channel 202 and at least another predetermined type of cells not to permeate between the corresponding chamber 206 and the channel 202. The barrier 209 can also allows no cells to permeate at all. Thus, the barrier 209 has a selective porosity for the cells and functions as a filter as well.

The bioreactor 200 also includes a biocompatible coating layer 205 applied to the channel walls, wherein the biocompatible coating layer 205 comprises a material that may inhibit cell adhesion to the biocompatible coating layer to keep the fluid communication in the channel 202 open. Alternatively, in place of the biocompatible coating layer 205, other means such as a leaky light guide can be utilized.

The bioreactor 200 may further include a biocompatible coating layer 207 applied to the sidewalls 266 of a chamber 206. The biocompatible coating layer 207 comprises a material that may inhibit cell adhesion to the biocompatible coating layer 207, enhance cell adhesion to the biocompatible coating layer 207, or function as a fluorescent marker or indicator of the state of cells. Different chambers 206 may have same or different coating layers.

The bioreactor 200 further includes at least one or more auxiliary ports 214 and corresponding auxiliary channels 214a. As formed, an auxiliary channel 214a is in fluid communication with a corresponding auxiliary port 214 and a corresponding chamber 206 for allowing individual control of the environment of the corresponding chamber 206. The individual control of the environment of the corresponding chamber 206 includes any and all intended activities that may affect the environment of a chamber such as the delivery or removal of the cells, fluids or chemicals to the corresponding chamber 206 or flushing the corresponding chamber 206.

Figure 2:
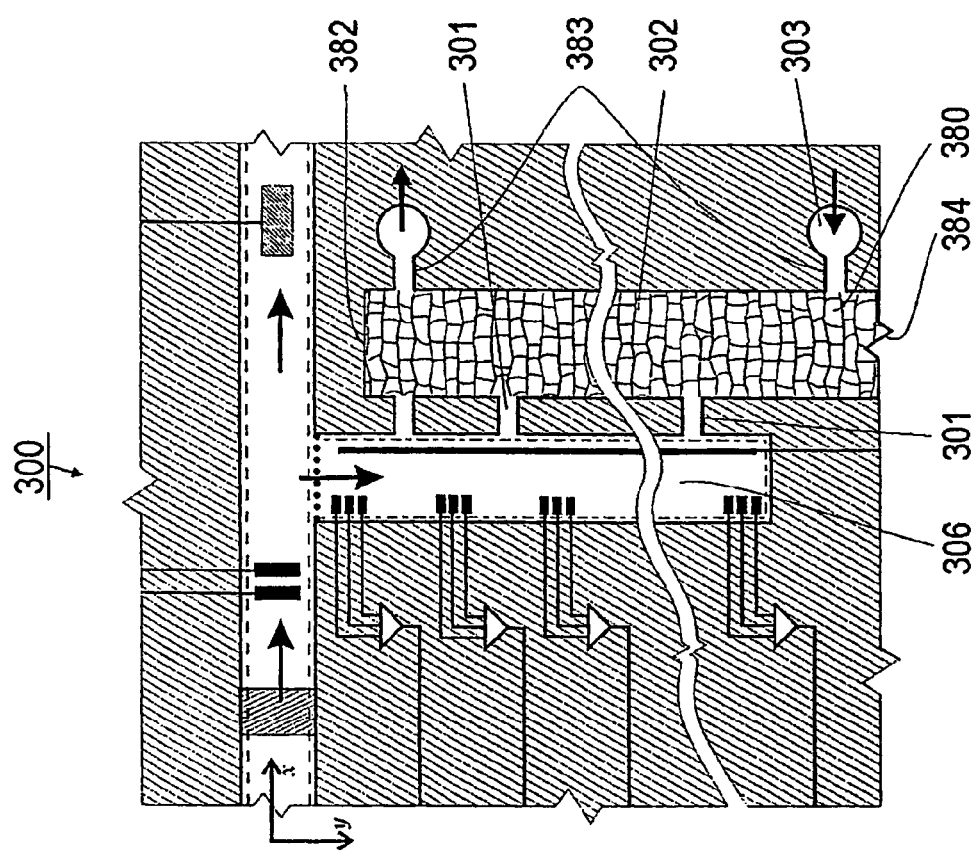
FIG. 2 shows a cross-sectional partial view of a bioreactor with a common feed line according to another embodiment of the present invention.

In an alternative embodiment as shown in FIG. 2, a bioreactor 300 includes at least one sample chamber 302 and a plurality of sample channels 301, wherein the plurality of sample channels 301 are in fluid communication with the sample chamber 302 and a corresponding chamber 306. As formed, the sample chamber 302 is in fluid communication with at least one corresponding auxiliary channel 383 that is in fluid communication with at least one corresponding auxiliary port 303, for allowing individual control of the environment of the corresponding sample chamber 302. The individual control of the environment of the corresponding sample chamber 302 includes any and all intended activities that may affect the environment of a sample chamber 302 such as the delivery or removal of the fluids, or materials, or substance such as chemicals to the corresponding sample chamber 302. The sample chamber 302 is further adapted for receiving a sample 380 of host material, such as soil, that provides exudates affecting the cells or biofilm in the corresponding chamber 306. The sample chamber 302 is also formed with a closed end 382 and an opposite open end 384 through which the host material can be received into or removed from the sample chamber 302. Additionally, a lid (not shown) adapted for slidably covering or opening the open end 384 of the sample chamber 302 can be utilized. This type of the bioreactor according to the embodiment of the present invention in FIG. 2 allows one to, among other things, observe, detect, adjust, control, and/or utilize the effects of exudates from a sample of host material on the cells growing in the chamber of the bioreactor.

Figure 4:
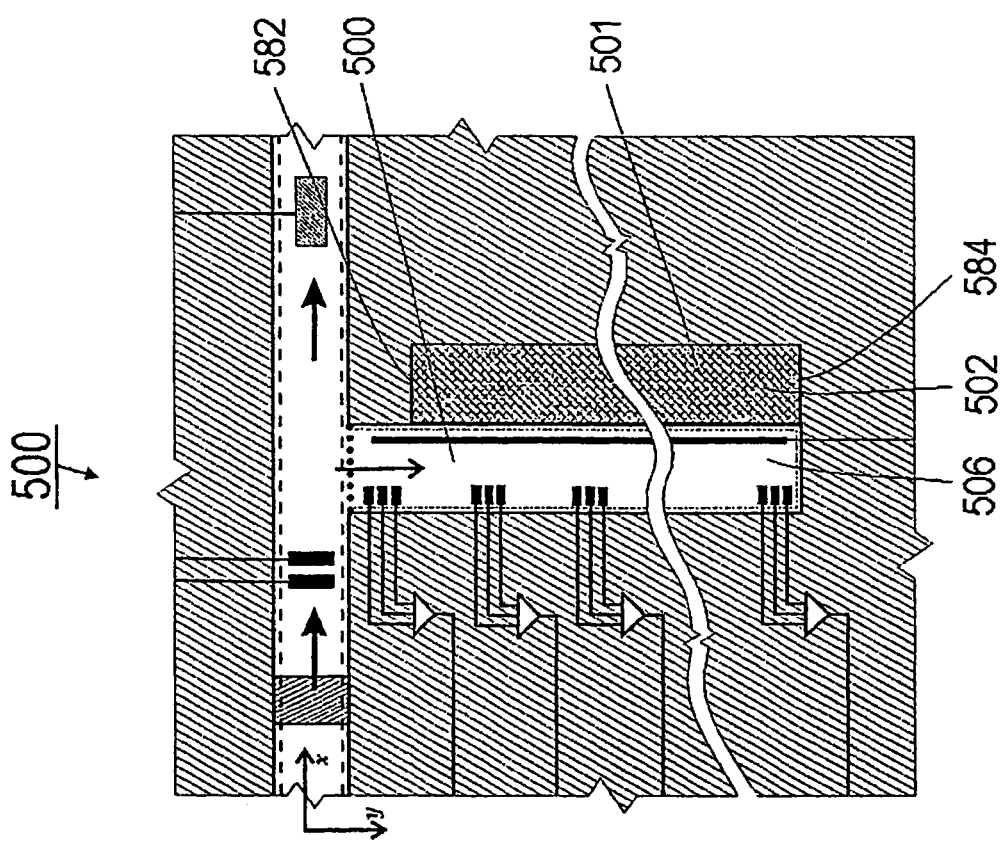
FIG. 4 shows a cross-sectional partial view of a bioreactor with a common feed line according to a further embodiment of the present invention.

In another alternative embodiment as shown in FIG. 4, a bioreactor 500 includes at least one sample chamber 502 that is formed in fluid communication with a corresponding chamber 506. The sample chamber 502 is adapted for receiving a sample of host material 501 that can directly affect the cells or biofilm in the corresponding chamber 506 because the sample chamber 502 is directly in fluid communication with a corresponding chamber 506. The sample chamber 502 is formed with a closed end 582 and an opposite open end 584 through which the sample of host material 501 can be received into or removed from the sample chamber 502. Additionally, a lid (not shown) adapted for slidably covering or opening the open end 584 of the sample chamber 502 can be utilized. This type of the bioreactor according to the embodiment of the present invention in FIG. 4 allows one to, among other things, observe, detect, adjust, control, and/or utilize the effects of a sample of host material on the cells growing in the chamber of the bioreactor.

The bioreactor 200 additionally includes, referring now to FIGS. 1A and 1D, means adapted for electrochemical measurements of the cells responsive to the liquid medium in at least one of the chambers 206. In one embodiment, the means for electrochemical measurements includes a counter electrode 211, a reference electrode 212, and a plurality of electrically conductive leads. Among the plurality of electrically conductive leads, a first electrically conductive lead 272a electrically couples the reference electrode 212 to a corresponding edge connector pad (not shown), and a second electrically conductive lead 272b electrically couples the counter electrode 211 to a corresponding edge connector pad (not shown). The means for electrochemical measurements can also be used to measure the electrochemical constituents outside the cells that reflect the status of the cells, the culture medium, or the cellular exudates.

The means for electrochemical measurements further includes a plurality of individually addressable working electrodes 270 and a plurality of corresponding amplifiers 210. Each individually addressable working electrode 270 is electrically coupled to a corresponding amplifier 210 through a corresponding electrically conductive lead 272. The bioreactor 200 further includes a plurality of electrically conductive output leads 274, each electrically coupling a corresponding amplifier 210 to an output device such as a multiplexed potentiostat (not shown).

In operation, the liquid medium being introduced into an array 204 through a corresponding channel 202 (and into one or more chambers 206) may include one or more analytes, and the plurality of individually addressable working electrodes 270 are adapted for capable of sensing the concentration of a single analyte of the liquid medium at multiple locations in a corresponding chamber 206 or the concentrations of a plurality of analytes of the liquid medium at multiple locations in the corresponding chamber 206 at a time period shorter than a characteristic reaction time related to at least one of cellular physiological activities of the cells. The plurality of individually addressable working electrodes 270 are further adapted for capable of measuring the metabolic variables related to the cells responsive to the liquid medium at multiple locations in the corresponding chamber 206 at a time period shorter than a characteristic reaction time related to at least one of cellular physiological activities of the cells.

Alternatively, as shown in FIG. 3, a bioreactor 400 has a plurality of controlling ports 404 and a plurality of connection channels 494, wherein each of the connection channels 494 is in fluid communication with a corresponding controlling port 404 and a chamber 496. The bioreactor 400 further includes a fluid control valve 402 adapted for controlling the fluid communication between the plurality of controlling ports 404 and the chamber 496, wherein the fluid control valve 402 includes a pneumatic or mechanical valve. A control port 401 adapted for controlling the fluid control valve 402 can also be provided.

In this embodiment, the counter electrode 405 and the reference electrode 406 are positioned between the fluid control valve 402 and the plurality of controlling ports 404, wherein the liquid medium includes at least one or more analytes, and wherein the plurality of individually addressable working electrodes are positioned between the fluid control valve 402 and the plurality of controlling ports 404 and adapted for capable of sensing the concentration of a single analyte of the liquid medium corresponding to multiple locations in a corresponding chamber 496 or the concentrations of a plurality of analytes of the liquid medium corresponding to multiple locations in the corresponding chamber 496 at a time period shorter than a characteristic reaction time related to at least one of cellular physiological activities of the cells. The plurality of individually addressable working electrodes are further adapted for capable of measuring the metabolic variables related to the cells responsive to the liquid medium at multiple locations corresponding to the corresponding chamber 496 at a time period shorter than a characteristic reaction time related to at least one of cellular physiological activities of the cells. This type of the bioreactor according to the embodiment of the present invention in FIG. 3 allows one to, among other things, minimize disturbances such as biofouling of the sensors to the cells in the chamber because the sensors are physically separated from the chamber of the bioreactor.

Figure 5:
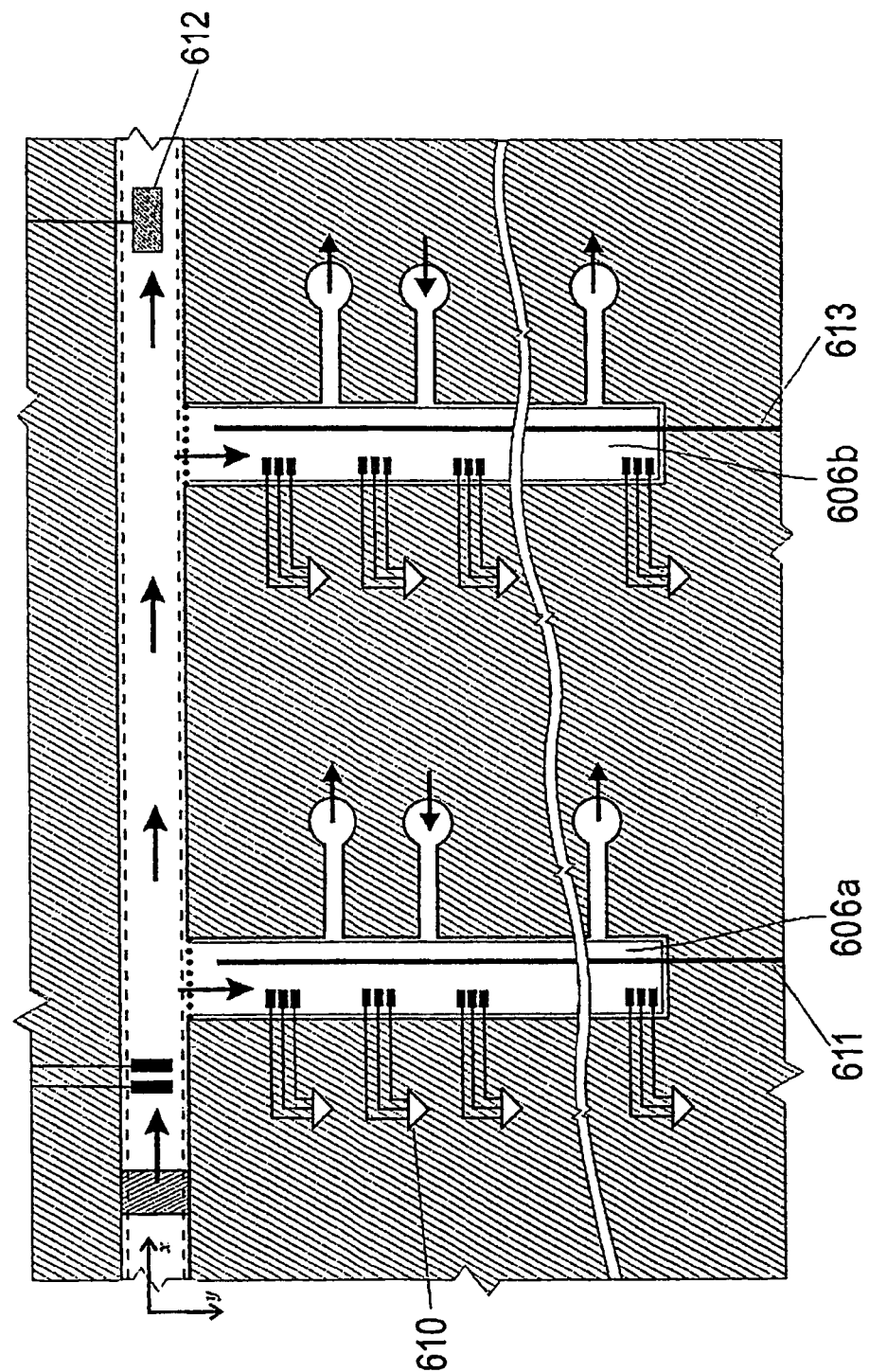
FIG. 5 shows a cross-sectional partial view of a bioreactor with a common feed line according to a yet another single-array embodiment of the present invention.

In another embodiment as shown in FIG. 5, the reference electrode 612 can be strategically positioned as a common reference electrode and adapted for electrochemical measurements of the cells responsive to the liquid medium in the plurality of chambers. Correspondingly, in each of the plurality of chambers, a counter electrode is adapted for electrochemical measurements of the cells responsive to the liquid medium in a corresponding chamber to allow the plurality of chambers to be operated individually and the means for electrochemical measurements for the plurality of chambers to be activated for one or more chambers at a time sequentially. For examples, a counter electrode 611 is adapted for electrochemical measurements of the cells responsive to the liquid medium in a corresponding chamber 606a, and a counter electrode 613 is adapted for electrochemical measurements of the cells responsive to the liquid medium in a corresponding chamber 606a, respectively.

The bioreactor of this invention further includes means positioned in the channel and adapted for monitoring of the cells therein optically, electrically or both. In one embodiment as shown in FIGS. 1A and 1B, the means for monitoring of the cells can include at least one optical sensor 213 and at least one lead 276 in optical communication with a corresponding optical sensor 213. The optical sensor 213 includes at least one device selected from the group of an LED and photodiode pair, a fiber optic coupler, and an optical detecting head. Other optical devices can be utilized as well. Alternatively, the means for monitoring of the cells includes at least one electrical sensor 213 and at least one lead 276 in electrical communication with a corresponding electrical sensor 213. Such monitoring means can also be utilized to monitor other dynamic activities in the channel, for example, activities and responses of cells when a bolus 208 of selected chemicals moves along the channel 202, which is adapted for allowing such movement of material along the channel 202.

The bioreactors of this invention can find many applications. In addition to applications set forth elsewhere and among other things, they can be utilized for culturing, studying and observing a plurality of biofilms simultaneously, where each biofilm may contain a predetermined type of cells that are same or different from other biofilms. Each array can receive one or more collection of cells in one or more chambers to grow. A bolus of selected chemicals or other substances, same or different for different arrays, can be introduced to move along a corresponding channel for each array of chambers. And a spectrum of dynamic properties due to the interfacing between the cells and the bolus of selected chemicals or other substances can be observed, detected, collected, analyzed and utilized.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the Claims. Furthermore, the embodiments described above are only intended to illustrate the principles of the present invention and are not intended to limit the claims to the disclosed elements. Indeed, since many embodiments of the invention can be made without departing from the spirit and scope of the invention, the invention resides in the claims hereinafter appended.

LIST OF REFERENCES

1. Godbey, W. T. and Atala, A., In Vitro Systems for Tissue Engineering, Ann. N.Y., Acad.Sci., 961, 10-26, 2002.
2. Murdin, A. D., Thorpe, J. S., Kirkby, N., Groves, D. J., Spier, R. E., Immobilisation and Growth of Hybridomas in Packed Beds, In: Bioreactors and biotransformations, Moody, G. W. and Baker, P. B., eds. Elsevier Applied Science Publishers, London, N.Y., 99-110, 1987.
3. De Bartolo, L., Jarosch-Von Schweder, G., Haverich, A., Bader, A., A Novel Full-Scale Flat Membrane Bioreactor Utilizing Porcine Hepatocytes: Cell Viability and Tissue-Specific Functions, Biotechnol. Prog., 16, 102-108, 2000.
4. McDuffie, N. G., Cell Culture Bioreactors. In: Bioreactor Design Fundamentals, Butterworth-Heinemann, Boston, 93-119, 1991.
5. Drioli, E, et al., Biocatalytic Membrane Reactors, Applications in Biotechnology and the Pharmaceutical Industry, Taylor & Francis, London, Pa., 1999.
6. Labecki, M., Bowen, B. D., Piret, J. M., Protein Transport in Ultrafiltration Hollow-Fiber Bioreactors for Mammalian Cell Culture, In: Membrane Separations in Biotechnology, Wang, W. K., ed., M. Dekker, New York, 1-62, 2001.
7. Nollert, M. U., Diamond, S. L., McIntire, L. V., Hydrodynamic Shear-Stress and Mass-Transport Modulation of Endothelial-Cell Metabolism, Biotechnol. Bioeng., 38, 588-602, 1991.
8. Augenstein, D. C., Sinskey, A. J., Wang, D. I. C., Effect of Shear on Death of Two Strains of Mammalian Tissue Cells, Biotechnol. Bioeng., 13, 409-418, 1971.
9. Millward, H. R., Bellhouse, B. J., Sobey, I. J., The Vortex Wave Membrane Bioreactor: Hydrodynamics and Mass Transfer, Chemical Engineering Journal and the Biochemical Engineering Journal, 62, 175-181, 1996.
10. Beeton, S., Bellhouse, B. J., Knowles, C. J., Millward, H. R., Nicholson, A. M., Wyatt, J. R., A Novel Membrane Bioreactor for Microbial-Growth, Appl. Microbiol. Bioteclmol., 40, 812-817, 1994.
11. Hu, W. S. and Aunins, J. G., Large-Scale Mammalian Cell Culture, Curr. Opin. Biotechnol., 8, 148-153, 1997.
12. Tobert, W. R., Lewis, C. Jr., White, P. J., Feder, J., Perfusion Culture Systems for Production of Mammalian Cell Biomolecules, In: Large-Scale Mammalian cell culture, Feder, J. and Tolbert, W. R., eds., Academic Press, Orlando, 97-123, 1985.
13. Voisard, D., Meuwly, F., Ruffieux, P. A., Baer, G., Kadouri, A., Potential of Cell Retention Techniques for Large-Scale High-Density Perfusion Culture of Suspended Mammalian Cells, Biotechnol. Bioeng., 82, 751-765, 2003.
14. MacNeill, B. D., Pomerantseva, I., Lowe, H. C., Oesterle, S. N., Vacanti, J. P., Toward a New Blood Vessel, Vasc. Med., 7, 241-246, 2002.
15. Wu, H. K., Odom, T. W., Chiu, D. T., Whitesides, G. M., Fabrication of Complex Three-Dimensional Microchannel Systems in PDMS, J. Am. Chem. Soc., 125, 554-559, 2003.
16. Griffith, L. G., Emerging Design Principles in Biomaterials and Scaffolds for Tissue Engineering, Reparative Medicine: Growing Tissues and Organs, 961, 83-95, 2002.
17. Snyder, J. D. and Desai, T. A., Fabrication of Multiple Microscale Features on Polymer Surfaces for Applications in Tissue Engineering, Biomedical Microdevices, 3, 293-300, 2001.
18. Solan, A., Prabhakar, V., Niklason, L., Engineered Vessels: Importance of the Extracellular Matrix, Transplant. Proc., 33, 66-68, 2001.
19. Griffith, L. G. and Naughton, G., Tissue Engineering—Current Challenges and Expanding Opportunities, Science, 295, 1009-+, 2002.
20. Powers, M. J., Domansky, K., Kaazempur-Mofrad, M. R., Kalezi, A., Capitano, A., Upadhyaya, A., Kurzawski, P., Wack, K. E., Stolz, D. B., Kamm, R., Griffith, L. G., A Microfabricated Array Bioreactor for Perfused 3D Liver Culture, Biotechnol. Bioeng., 78, 257-269, 2002.
21. Park, T. H. and Shuler, M. L, Integration of Cell Culture and Microfabrication Technology, Biotechnol. Prog., 19, 243-253, 2003.
22. Borenstein, J. T., Terai, H., King, K. R., Weinberg, E. J., Kaazempur-Mofrad, M. R., Vacanti, J. P., Microfabrication Technology for Vascularized Tissue Engineering, Biomedical Microdevices, 4, 167-175, 2002.
23. Kaihara, S., Borenstein, J., Koka, R., Lalan, S., Ochoa, E. R., Ravens, M., Pien, H., Cunningham, B., Vacanti, J. P., Silicon Micromachining to Tissue Engineer Branched Vascular Channels for Liver Fabrication, Tissue Eng., 6, 105-117, 2000.
24. Allen, J. W. and Bhatia, S. N., Improving the Next Generation of Bioartificial Liver Devices, Seminars in Cell & Developmental Biology, 13, 447-454, 2002.
25. Passeraub, P. A, Almeida, A. C., Thakor, N. V., Design, Microfabrication and Analysis of a Microfluidic Chamber for the Perfusion of Brain Tissue Slices, Biomedical Microdevices, 5, 147-155, 2003.
26. Fink, C., Ergun, S., Kralisch, D., Remmers, U., Weil, J., Eschenhagen, T., Chronic Stretch of Engineered Heart Tissue Induces Hypertrophy and Functional Improvement, FASEB J., 14, 669-679, 2000.
27. Mooney, D. T., Mazzoni, C. L., Breuer, C., McNamara, K., Hem, D., Vacanti, J. P., Langer, R., Stabilized Polyglycolic Acid Fibre Based Tubes for Tissue Engineering, Biomaterials, 17, 115-124, 1996.
28. Boyden, S., The Chemotactic Effect of Mixtures of Antibody and Antigen on Polymorphonuclear Leucocytes, J. Exp. Med., 115, 453-466, 1962.
29. Harvath, L., Falk, W., Leonard, E. J., Rapid Quantitation of Neutrophil Chemotaxis—Use of A Polyvinylpyrrolidone-Free Polycarbonate Membrane in A Multiwell Assembly, J. Immunol. Methods, 37, 39-45, 1980.
30. Falk, W., Goodwin, R. H., Leonard, E. J., A 48-Well Micro Chemotaxis Assembly for Rapid and Accurate Measurement of Leukocyte Migration, J. Immunol. Methods, 33, 239-247, 1980.
31. Yao, J., Harvath L., Gilbert, D. L., Colton, C. A., ChemotaxisbyA Cns Macrophage, the Microglia, J. Neurosci. Res., 27, 36-42, 1990.
32. Roth. S. J., Carr, M. W., Rose, S. S., Springer, T. A., Characterization of Transendothelial Chemotaxis of T Lymphocytes, J. Immunol. Methods, 188, 97-116, 1995.

33. Klemke, R. L., Leng, J., Molander, R., Brooks, P. C., Vuori, K., Cheresh, D. A., CAS/Crk Coupling Serves As a "Molecular Switch" for Induction of Cell Migration, Journal of Cell Biology, 140, 961-972, 1998.

34. Ding, Z., Xiong, K., Issekutz, T. B., Chemokines Stimulate Human T Lymphocyte Transendothelial Migration to Utilize VLA-4 in Addition to LFA-1, J.Leukoc.Biol., 69, 458-466, 2001.

35. Jones, D. A., Abbassi, O., McIntire, L. V., McEver, R. P., Smith, C. W., P-Selectin Mediates Neutrophil Rolling on Histamine-Stimulated Endothelial Cells, Biophys. J., 65, 1560-1569, 1993.

36. Brown, D. and Larson, R., Improvements to Parallel Plate Flow Chambers to Reduce Reagent and Cellular Requirements, BMC Immunology, 2, 9-16, 2001.

37. Cinamon, G. and Alon, R., A Real Time in Vitro Assay for Studying Leukocyte Transendothelial Migration Under Physiological Flow Conditions, J. Immunol. Methods, 273, 53-62, 2003.

38. Renard, M., Heutte, F., Boutherin-Falson, O., Finet, M., Boisseau, M. R., Induced Changes of Leukocyte Slow Rolling in an in Flow Pharmacological Model of Adhesion to Endothelial Cells, Biorheology, 40, 173-178, 2003.

39. Munn, L. L., Melder, R. J., Jain, R. K., Analysis of Cell Flux in the Parallel-Plate Flow Chamber—Implications for Cell Capture Studies, Biophys. J., 67, 889-895, 1994.

40. Ley, K., The Selectins As Rolling Receptors. In: The selecting: initiators of leukocyte endothelial adhesion, Vestweber, D, ed. Harwood Academic Publishers, Australia, 63-104, 1997.

41. Papadaki, M. and Mcintire, L. V., Quantitative Measurement of Shear-Stress Effects on Endothelial Cells. In: Tissue engineering methods and protocols, Morgan, J. R. and Yarmush, M. L, eds. Humana Press, Totowa, N.J., 577-593, 1999.

42. Ramos, C. L. and Lawrence, M. B., Quantitative Measurement of Cell-Cell Adhesion Under Flow Conditions, In: Tissue engineering methods and protocols, Morgan, J. R. and Yarmush, M. L., eds. Humana Press, Totowa, N.J., 507-519, 1999.

43. Hamner, D. A. and Brunk, D. K., Measuring Receptor-Mediated Cell Adhesion Under Flow: Cell-Free Systems. In: Tissue engineering methods and protocols, Morgan, J. R. and Yarmush, M. L., eds. Humana Press, Totowa, N.J., 543-552, 1999.

44. Jain, R. K., Munn, L. L., Fukumura, D., Melder, R. J., In Vitro and In Vivo Quantification of Adhesion Between Leukocytes and Vascular Endothelium. In: Tissue engineering methods and protocols, Morgan, J. R. and Yarmush, M. L., eds. Humana Press, Totowa, N.J., 553-575, 1999.

45. Li, C. Y., Shan, S., Huang, Q., Braun, R. D., Lanzen, J., Hu, K., Lin, P., Dewhirst, M. W., Initial Stages of Tumor Cell-Induced Angiogenesis: Evaluation Via Skin Window Chambers in Rodent Models, J Natl Cancer Inst, 92, 143-7, 2000.

46. Jain, R. K., Munn, L. L., Fukumura, D., Dissecting Tumour Pathophysiology Using Intravital Microscopy. Nat Rev Cancer, 2, 266-76, 2002.

47. Jain, R. K., Munn, L. L, Fukumura, D., Dissecting Tumour Pathophysiology Using Intravital Microscopy. Nature Reviews Cancer, 2, 266-276, 2002.

48. Jain, R. K., Angiogenesis and Lymphangiogenesis in Tumors: Insights From Intravital Microscopy, Cold Spring Harb.Symp.Quant.Biol., 67, 239-248, 2002.

49. Follcman, J., Bach, M., Rowe, J. W., Davidoff, F., Lambert, P., Hirsch, C., Goldberg, A., Hiatt, H. H., Glass, J., Henshaw, E., Tumor Angiogenesis—Therapeutic Implications, N. Engl. J. Med., 285, 1182-1186, 1971.

50. Weidner, N., Semple, J. P., Welch, W. R., Folkman, J., Tumor Angiogenesis and Metastasis—Correlation in Invasive Breast-Carcinoma, N. Engl. J. Med., 324, 1-8, 1991.

51. Lin, P., Buxton, J. A, Acheson, A, Radziejewsli, C, Maisonpierre, P. C., Yancopoulos, G. D., Channon, K. M., Hale, L. P., Dewhirst, M. W., George, S. E., Peters, K. G., Antiangiogenic Gene Therapy Targeting the Endothelium-Specific Receptor Tyrosine Kinase Tie2, Proc. Natl Acad Sci U S A, 95, 8829-34, 1998.

52. Lin, P., Polverini, P., Dewhirst, M., Shan, S., Rao, P. S., Peters, K., Inhibition of Tumor Angiogenesis Using a Soluble Receptor Establishes a Role for Tie2, in Pathologic Vascular Growth, J Clin Invest, 100, 2072-8, 1997.

53. Lin, P., Sankar, S., Shan, S., Dewhirst, M. W., Polverini, P. J., Quinn, T. Q., Peters, K. G., Inhibition of Tumor Growth by Targeting Tumor Endothelium Using a Soluble Vascular Endothelial Growth Factor Receptor, Cell Growth Differ, 9, 49-58, 1998.

54. Heidemann, J., Ogawa, H., Dwinell, M. B., Rafiee, P., Maaser, C., Gockel, H. R., Otterson, M. F., Ota, D. M., Lugering, N., Domschke, W., Binion, D. G., Angiogenic Effects of Interleukin 8 (CXCL8) in Human Intestinal Microvascular Endothelial Cells Are Mediated by CXCR2, J.Biol.Chem., 278, 8508-8515, 2003.

55. Li, Y., Tondravi, M., Liu, J., Smith, E., Haudenschild, C. C., Kaczmarek, M., Zhan, X., Cortactin Potentiates Bone Metastasis of Breast Cancer Cells, Cancer Res, 61, 6906-11, 2001.

56. Higgs, H. N. and Pollard, T. D., Regulation of Actin Filament Network Formation Through Arp2/3 Complex: Activation by a Diverse Array of Proteins, Annu. Rev. Biochem., 70, 649-676, 2001.

57. Li, F. Y., Zhang, L, Metzger, R. M., On the Growth of Highly Ordered Pores in Anodized Aluminum Oxide, Chem. Mater., 10, 2470-2480, 1998.

58. Li, A. P., Muller, F., Birner, A., Nielsch, K., Gosele, U., Hexagonal Pore Arrays With a 50-420 Nm Interpore Distance Formed by Self-Organization in Anodic Alumina, J. Appl. Phys., 84, 6023-6026, 1998.

59. Black, C. T., Guarini, K. W., Milkove, K. R., Baker, S. M., Russell, T. P., Tuominen, M. T., Integration of Self-Assembled Diblock Copolymers for Semiconductor Capacitor Fabrication, Appl.Phys.Lett., 79, 409-411, 2001.

60. Black, C. T. and Guarini, K. W., Diblock Copolymers: Self-Assembly for Applications in Microelectronics, In: Encyclopedia of Materials:Science and Technology, Buschow, K H J, ed. Elsevier, N.Y., 1-6, 2002.

61. Guarini, K. W., Black, C. T., Zhang, Y., Kim, H., Sikorski, E. M., Babich, I. V., Process Integration of Self-Assembled Polymer Templates into Silicon Nanofabrication, Journal of Vacuum Science & Technology B, 20, 2788-2792, 2002.

62. MartinezZaguilan, R., Seftor, E. A., Seftor, R. E. B., Chu, Y. W., Gillies, R. J., Hendrix, M. J. C., Acidic PH Enhances the Invasive Behavior of Human Melanoma Cells, Clinical & Experimental Metastasis, 14, 176-186, 1996.

63. Gillies, R. J., Raghunand, N., Karczmar, G. S., Bhujwalla, Z. M., MRI of the Tumor Microenvironment, J.Magn.Reson.Imaging, 16, 430-450, 2002.

64. Bhujwalla, Z. M., Artemov, D., Ballesteros, P., Cerdan, S., Gillies, R. J., Solaiyappan, M, Combined Vascular and Extracellular PH Imaging of Solid Tumors, NMR Biomed., 15, 114-119, 2002.

65. Helmlinger, G., Schell, A., Dellian, M., Forbes, N. S., Jain, R. K., Acid Production in Glycolysis-Impaired Tumors Provides New Insights into Tumor Metabolism, Clin.Cancer Res., 8, 1284-1291, 2002.

What is claimed is:

1. A bioreactor comprising:
   (a) a substrate having a first surface and an opposite second surface, defining a channel therein;
   (b) a plurality of chambers formed in the substrate, wherein each of the plurality of chambers is adapted for receiving and culturing at least one predetermined type of cells in a liquid medium and formed with an open end, an opposite closed end and side walls, the open end and the closed end defining a depth, d, therebetween for the corresponding chamber, the sidewalls defining a width, w, therebetween for the corresponding chamber, and the chamber being in fluid communication with the channel through the open end;
   (c) means adapted for electrochemical measurements of the cells responsive to the liquid medium in at least one of the chambers; and
   (d) a barrier for at least one of the chambers, wherein the barrier:
      (i) is positioned at the open end of the corresponding chamber and proximate to the intersection of the channel and the corresponding chamber; and
      (ii) has a porosity to allow the corresponding chamber and the channel to be in fluid communication, and to allow at least one predetermined type of cells to permeate between the corresponding chamber and the channel and at least another predetermined type of cells not to permeate between the corresponding chamber and the channel,
      wherein the corresponding chamber defined between the open end and opposite closed end is formed substantially perpendicular to the channel and configured not to allow a liquid medium to pass through the open end and opposite closed end through the channel, and
      wherein the means for electrochemical measurements comprises a plurality of electrically individually addressable working electrodes arranged along the corresponding chamber between the open end and opposite closed end such that none of the electrodes are arranged along the channel.

2. The bioreactor of claim 1, wherein at least two of the plurality of chambers have depths or widths same or different from each other.

3. The bioreactor of claim 1, further comprising an inlet port in fluid communication with the channel, and an outlet port in fluid communication with the channel, wherein the inlet port and the outlet port are apart from each other along the channel.

4. The bioreactor of claim 1, wherein the cells are in the form of a biofilm.

5. The bioreactor of claim 1, wherein the cells comprise bacteria.

6. The bioreactor of claim 1, wherein the cells comprise protozoa.

7. The bioreactor of claim 1, further comprising a biocompatible coating layer applied to the channel walls.

8. The bioreactor of claim 7, wherein the biocompatible coating layer comprises a material that may inhibit cell adhesion to the biocompatible coating layer.

9. The bioreactor of claim 1, further comprising a biocompatible coating layer applied to the sidewalls of each chamber.

10. The bioreactor of claim 9, wherein the biocompatible coating layer comprises a material that may inhibit cell adhesion to the biocompatible coating layer, enhance cell adhesion to the biocompatible coating layer, or function as a fluorescent marker or indicator of the state of cells.

11. The bioreactor of claim 1, further comprising at least one auxiliary port and an auxiliary channel in fluid communication with the auxiliary port and a corresponding one of the chambers for allowing individual control of the environment of the corresponding chamber.

12. The bioreactor of claim 11, wherein the individual control of the environment of the corresponding chamber includes delivery or removal of the cells, fluids or chemicals to the corresponding chamber or flushing the corresponding chamber.

13. The bioreactor of claim 11, further comprising at least one sample chamber and a plurality of sample channels in fluid communication with the sample chamber and a corresponding chamber, wherein the sample chamber is in fluid communication with at least one corresponding auxiliary channel that is in fluid communication with at least one corresponding auxiliary port, for allowing individual control of the environment of the corresponding sample chamber.

14. The bioreactor of claim 13, wherein the individual control of the environment of the corresponding sample chamber includes delivery or removal of the fluids or chemicals to the corresponding sample chamber.

15. The bioreactor of claim 13, wherein the sample chamber is adapted for receiving a sample of host material that provides exudates affecting the cells or biofilm in the corresponding chamber.

16. The bioreactor of claim 15, wherein the sample chamber is formed with a closed end and an opposite open end through which the host material can be received into or removed from the sample chamber.

17. The bioreactor of claim 16, further comprising a lid adapted for slidably covering or opening the open end of the sample chamber.

18. The bioreactor of claim 16, wherein the host material comprises soil.

19. The bioreactor of claim 1, further comprising at least one sample chamber in fluid communication with a corresponding chamber.

20. The bioreactor of claim 19, wherein the sample chamber is adapted for receiving a sample of host material that affects the cells or biofilm in the corresponding chamber.

21. The bioreactor of claim 20, wherein the sample chamber is formed with a closed end and an opposite open end through which the host material can be received into or removed from the sample chamber.

22. The bioreactor of claim 21, further comprising a lid adapted for slidably covering or opening the open end of the sample chamber.

23. The bioreactor of claim 1, wherein the substrate is fabricated from glass, Mylar, PDMS, silicon, a polymer, a semiconductor, or any combination of them.

24. The bioreactor of claim 1, wherein the means for electrochemical measurements comprises:
   (i) a counter electrode;
   (ii) a reference electrode; and
   (iii) a plurality of electrically conductive leads, where a first electrically conductive lead electrically couples the reference electrode to a corresponding edge connector pad, and a second electrically conductive lead electrically couples the counter electrode to a corresponding edge connector pad.

25. The bioreactor of claim 24, wherein the means for electrochemical measurements further comprises:
(iv) a plurality of corresponding amplifiers, wherein each individually addressable working electrode is electrically coupled to a corresponding amplifier through a corresponding electrically conductive lead.

26. The bioreactor of claim 25, wherein the liquid medium comprises at least one analyte, and wherein the plurality of individually addressable working electrodes are adapted for capable of sensing the concentration of a single analyte of the liquid medium at multiple locations in a corresponding chamber or the concentrations of a plurality of analytes of the liquid medium at multiple locations in the corresponding chamber at a time period shorter than a characteristic reaction time related to at least one of cellular physiological activities of the cells.

27. The bioreactor of claim 26, wherein the plurality of individually addressable working electrodes are further adapted for capable of measuring the metabolic variables related to the cells responsive to the liquid medium at multiple locations in the corresponding chamber at a time period shorter than a characteristic reaction time related to at least one of cellular physiological activities of the cells.

28. The bioreactor of claim 25, further comprising a plurality of electrically conductive output leads, each electrically coupling a corresponding amplifier to an output device.

29. The bioreactor of claim 28, wherein the output device comprises a multiplexed potentiostat.

30. The bioreactor of claim 25, further comprising a plurality of controlling ports and a plurality of connection channels, wherein each of the connection channels is in fluid communication with a corresponding controlling port and the chamber.

31. The bioreactor of claim 30, further comprising a fluid control valve adapted for controlling the fluid communication between the plurality of controlling ports and the chamber.

32. The bioreactor of claim 31, wherein the fluid control valve comprises a pneumatic or mechanical valve.

33. The bioreactor of claim 32, further comprising a control port adapted for controlling the fluid control valve.

34. The bioreactor of claim 32, wherein the counter electrode and the reference electrode are positioned between the fluid control valve and the plurality of controlling ports.

35. The bioreactor of claim 34, wherein the liquid medium comprises at least one analyte, and wherein the plurality of individually addressable working electrodes are positioned between the fluid control valve and the plurality of controlling ports and adapted for capable of sensing the concentration of a single analyte of the liquid medium corresponding to multiple locations in a corresponding chamber, or the concentrations of a plurality of analytes of the liquid medium corresponding to multiple locations in the corresponding chamber, at a time period shorter than a characteristic reaction time related to at least one of cellular physiological activities of the cells.

36. The bioreactor of claim 35, wherein the plurality of individually addressable working electrodes are further adapted for capable of measuring the metabolic variables related to the cells responsive to the liquid medium at multiple locations corresponding to the corresponding chamber, at a time period shorter than a characteristic reaction time related to at least one of cellular physiological activities of the cells.

37. The bioreactor of claim 24, wherein the reference electrode is adapted for electrochemical measurements of the cells responsive to the liquid medium in the plurality of chambers.

38. The bioreactor of claim 24, wherein in each of the plurality of chambers, a counter electrode is adapted for electrochemical measurements of the cells responsive to the liquid medium in a corresponding chamber to allow the plurality of chambers to be operated individually and the means for electrochemical measurements for the plurality of chambers to be activated for one or more chambers at a time sequentially.

39. The bioreactor of claim 1, further comprising means positioned in the channel and adapted for monitoring of the cells therein.

40. The bioreactor of claim 39, wherein the means for monitoring of the cells comprises at least one optical sensor and at least one lead in optical communication with a corresponding optical sensor.

41. The bioreactor of claim 40, wherein the optical sensor comprises at least one device selected from the group of an LED and photodiode pair, a fiber optic coupler, and an optical detecting head.

42. The bioreactor of claim 39, wherein the means for monitoring of the cells comprises at least one electrical sensor and at least one lead in electrical communication with a corresponding electrical sensor.

43. The bioreactor of claim 1, wherein the channel is adapted for allowing a bolus of selected chemicals to move along the channel.

44. A bioreactor comprising:
(a) a substrate having a first surface and an opposite second surface; and
(b) a plurality of arrays of chambers formed on the substrate, each array being adapted for receiving cells in a liquid medium and comprising a channel and a plurality of chambers formed in the substrate, wherein each of the plurality of chambers is adapted for receiving cells in a liquid medium and formed with an open end, an opposite closed end and side walls, the open end and the closed end defining a depth, d, therebetween for the corresponding chamber, the sidewalls defining a width, w, therebetween for the corresponding chamber, and the chamber being in fluid communication with the channel through the open end, wherein at least two of the plurality of chambers have depths same or different from each other, and wherein for at least one array, each of the chambers is adapted to receive and culture at least one predetermined type of cells;
(c) means adapted for electrochemical measurements of the cells responsive to the liquid medium in at least one of the chambers of at least one array; and
(d) a barrier for at least one of the chambers of at least one array, wherein the barrier:
(i) is positioned at the open end of the corresponding chamber proximate to the intersection of the channel and the corresponding chamber; and
(ii) has a porosity to allow the corresponding chamber and the channel to be in fluid communication, and to allow at least one predetermined type of cells to permeate between the corresponding chamber and the channel and at least another predetermined type of cells not to permeate between the corresponding chamber and the channel,
wherein the corresponding chamber defined between the open end and closed end is formed substantially perpendicular to the channel and configured not to allow a liquid medium to pass through the open end and opposite closed end through the channel, and wherein the means for electrochemical measurements comprises a plurality of individually addressable working electrodes arranged along the corresponding chamber between the open end and opposite closed end such that none of the electrodes are arranged along the channel.

45. The bioreactor of claim 44, wherein for at least one array of chambers at least two of the plurality of chambers have widths same or different from each other.

46. The bioreactor of claim 44, for at least one array of chambers, further comprising an inlet port in fluid communication with the channel, and an outlet port in fluid communication with the channel, wherein the inlet port and the outlet port are apart from each other along the channel.

47. The bioreactor of claim 44, wherein the cells are in the forms of a plurality of biofilms.

48. The bioreactor of claim 47, wherein the cells comprise bacteria.

49. The bioreactor of claim 47, wherein the cells comprise protozoa.

50. The bioreactor of claim 44, for at least one array of chambers, further comprising a biocompatible coating layer applied to the channel walls.

51. The bioreactor of claim 50, wherein the biocompatible coating layer comprises a material that may inhibit cell adhesion to the biocompatible coating layer.

52. The bioreactor of claim 44, for at least one array of chambers, further comprising a biocompatible coating layer applied to the sidewalls of each chamber.

53. The bioreactor of claim 52, wherein the biocompatible coating layer comprises a material that may inhibit cell adhesion to the biocompatible coating layer, enhance cell adhesion to the biocompatible coating layer, or function as a fluorescent marker or indicator of the state of cells.

54. The bioreactor of claim 44, for at least one array of chambers, further comprising at least one auxiliary port and an auxiliary channel in fluid communication with the auxiliary port and a corresponding one of the chambers for allowing individual control of the environment of the corresponding chamber.

55. The bioreactor of claim 54, wherein the individual control of the environment of the corresponding chamber includes delivery or removal of the cells, fluids or chemicals to the corresponding chamber or flushing the corresponding chamber.

56. The bioreactor of claim 44, wherein the substrate is fabricated from glass, Mylar, PDMS, silicon, a polymer, a semiconductor, or any combination of them.

57. The bioreactor of claim 44, wherein the means for electrochemical measurements comprises:
  (i) a counter electrode;
  (ii) a reference electrode; and
  (iii) a plurality of electrically conductive leads, where a first electrically conductive lead electrically couples the reference electrode to a corresponding edge connector pad, and a second electrically conductive lead electrically couples the counter electrode to a corresponding edge connector pad.

58. The bioreactor of claim 57, wherein the means for electrochemical measurements further comprises:
  (iv) a plurality of corresponding amplifiers, wherein each individually addressable working electrode is electrically coupled to a corresponding amplifier through a corresponding electrically conductive lead.

59. The bioreactor of claim 58, wherein the liquid medium comprises at least one analyte, and wherein the plurality of individually addressable working electrodes are adapted for capable of sensing the concentration of a single analyte of the liquid medium at multiple locations in a corresponding chamber or the concentrations of a plurality of analytes of the liquid medium at multiple locations in the corresponding chamber at a time period shorter than a characteristic reaction time related to at least one of cellular physiological activities of the cells.

60. The bioreactor of claim 59, wherein the plurality of individually addressable working electrodes are further adapted for capable of measuring the metabolic variables related to the cells responsive to the liquid medium at multiple locations in the corresponding chamber at a time period shorter than a characteristic reaction time related to at least one of cellular physiological activities of the cells.

61. The bioreactor of claim 58, further comprises a plurality of electrically conductive output leads, each electrically coupling a corresponding amplifier to an output device.

62. The bioreactor of claim 61, wherein the output device comprises a multiplexed potentiostat.

63. The bioreactor of claim 44, for at least one array of chambers, further comprising means positioned in the channel and adapted for monitoring of the cells therein.

64. The bioreactor of claim 63, wherein the means for monitoring of the cells comprises at least one optical sensor and at least one lead in optical communication with a corresponding optical sensor.

65. The bioreactor of claim 64, wherein the optical sensor comprises at least one device selected from the group of an LED and photodiode pair, a fiber optic coupler, and an optical detecting head.

66. The bioreactor of claim 63, wherein the means for monitoring of the cells comprises at least one electrical sensor and at least one lead in electrical communication with a corresponding electrical sensor.

67. The bioreactor of claim 64, wherein the channel is adapted for allowing a bolus of selected chemicals to move along the channel.

68. A method for culturing a plurality of biofilms, each containing a predetermined type of cells or cell growth conditions, comprising the steps of:
  (i) providing a bioreactor that has a substrate having a first surface and an opposite second surface and a plurality of arrays of chambers formed on the substrate, each array being adapted for receiving cells in a liquid medium and comprising a channel and a plurality of chambers formed in the substrate, wherein each of the plurality of chambers is adapted for receiving cells in a liquid medium and formed with an open end, an opposite closed end and side walls, the open end and the closed end defining a depth, d, therebetween for the corresponding chamber, the sidewalls defining a width, w, therebetween for the corresponding chamber, and the chamber being in fluid communication with the channel through the open end, wherein the corresponding chamber defined between the open end and opposite closed end is formed substantially perpendicular to the channel and configured not to allow a liquid medium to pass through the open end and opposite closed end through the channel, and wherein at least two of the plurality of chambers have depths different from each other; and
  (ii) culturing at least two biofilms in at least two arrays of chambers of the bioreactor.

69. The bioreactor of claim 68, further comprising the step of providing a bolus of selected chemicals to move along the channel for each of the at least two arrays of chambers.

* * * * *